(12) United States Patent
Goldshtein et al.

(10) Patent No.: US 11,465,974 B2
(45) Date of Patent: Oct. 11, 2022

(54) CRYSTALLINE POLYMORPHS OF PRACINOSTAT AND PRACINOSTAT SALTS

(71) Applicant: ASSIA CHEMICAL INDUSTRIES LTD., Petach Tikva (IL)

(72) Inventors: Jenny Goldshtein, Netaniya (IL); Maytal Piran, Rishon le Zion (IL); Doron Rudik, Modi'in (IL); Rotem Sella-Erez, Tel Aviv (IL); Sharona Alfasie Shachan-Tov, Kfar-Saba (IL); Ofir Shaul, Hod Hasharon (IL)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 20 days.

(21) Appl. No.: 16/954,227

(22) PCT Filed: Dec. 19, 2018

(86) PCT No.: PCT/US2018/066423
§ 371 (c)(1),
(2) Date: Jun. 16, 2020

(87) PCT Pub. No.: WO2019/126282
PCT Pub. Date: Jun. 27, 2019

(65) Prior Publication Data
US 2021/0087150 A1    Mar. 25, 2021

Related U.S. Application Data

(60) Provisional application No. 62/607,403, filed on Dec. 19, 2017, provisional application No. 62/638,376, filed on Mar. 5, 2018, provisional application No. 62/649,695, filed on Mar. 29, 2018.

(51) Int. Cl.
*C07D 235/08* (2006.01)

(52) U.S. Cl.
CPC ........ *C07D 235/08* (2013.01); *C07B 2200/13* (2013.01)

(58) Field of Classification Search
CPC ............................ C07D 235/08; C07B 2200/13
USPC ...................................................... 514/394
See application file for complete search history.

(56) References Cited

U.S. PATENT DOCUMENTS 6,627,646 B2 * 9/2003 Bakale ................... A61P 37/08
514/322

FOREIGN PATENT DOCUMENTS

WO    2007030080 A1    3/2007
WO    2017192451 A1    11/2017

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.,"J of Pharm. (Lahore), 1979, 1(1), 59-66.*
U.S. Pharmacopia #23, National Formulary#18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
Guillory (in Brittain ed.), polymorphism in Pharmaceutical Solids, 'NY: Marcel Dekker., 1-2, 183-226. (Year: 1999).*
Rodriguez-Spong et al., "General principles, etc.," Adv. Drug Delivery REviews 56 241-274. (Year: 2004).*
Haishan Wang et al: Discovery of (2 E)-3-{2-Butyl-1-[2-(diethylamino)ethyl]-1 H -benzimidazol-5-yl}-N-hydroxyacrylamide (SB939), an Orally Active Histone Deacetylase Inhibitor with a Superior Preclinical Profile, Journal of Medicinal Chemistry, vol. 54, No. 13, Jun. 2, 2011 (Jun. 2, 2011).
Caira Ed-Montchamp Jean-Luc: "Crystalline Polymorphism of Organic Compounds", Topics in Current Chemistry; [Topics in Current Chemistry], Springer, Berlin, DE, vol. 198, Jan. 1, 1998 (Jan. 1, 1998), pp. 163-208.
International Serach Report and Written Opinion of the International Searching Authority issued in corresponding International Appl. No. PCT/US2018/066423 dated Apr. 17, 2019 (21 pages).

* cited by examiner

*Primary Examiner* — Niloofar Rahmani
(74) *Attorney, Agent, or Firm* — Carter, DeLuca & Farrell LLP

(57) ABSTRACT

The present disclosure encompasses crystalline polymorphs of Pracinostat and of Pracinostat salts, and pharmaceutical compositions thereof.

7 Claims, 30 Drawing Sheets

Figure 1: A characteristic X-ray powder diffraction pattern (XRPD) of Pracinostat Form P1 (the peak at 28.45° is attributed to silicon powder added as an internal standard)

Figure 3: A characteristic X-ray powder diffraction pattern (XRPD) of Pracinostat Form P3

Figure 4: A characteristic X-ray powder diffraction pattern (XRPD) of Pracinostat Form P4

Figure 6: A characteristic X-ray powder diffraction pattern (XRPD) of Pracinostat Form P7

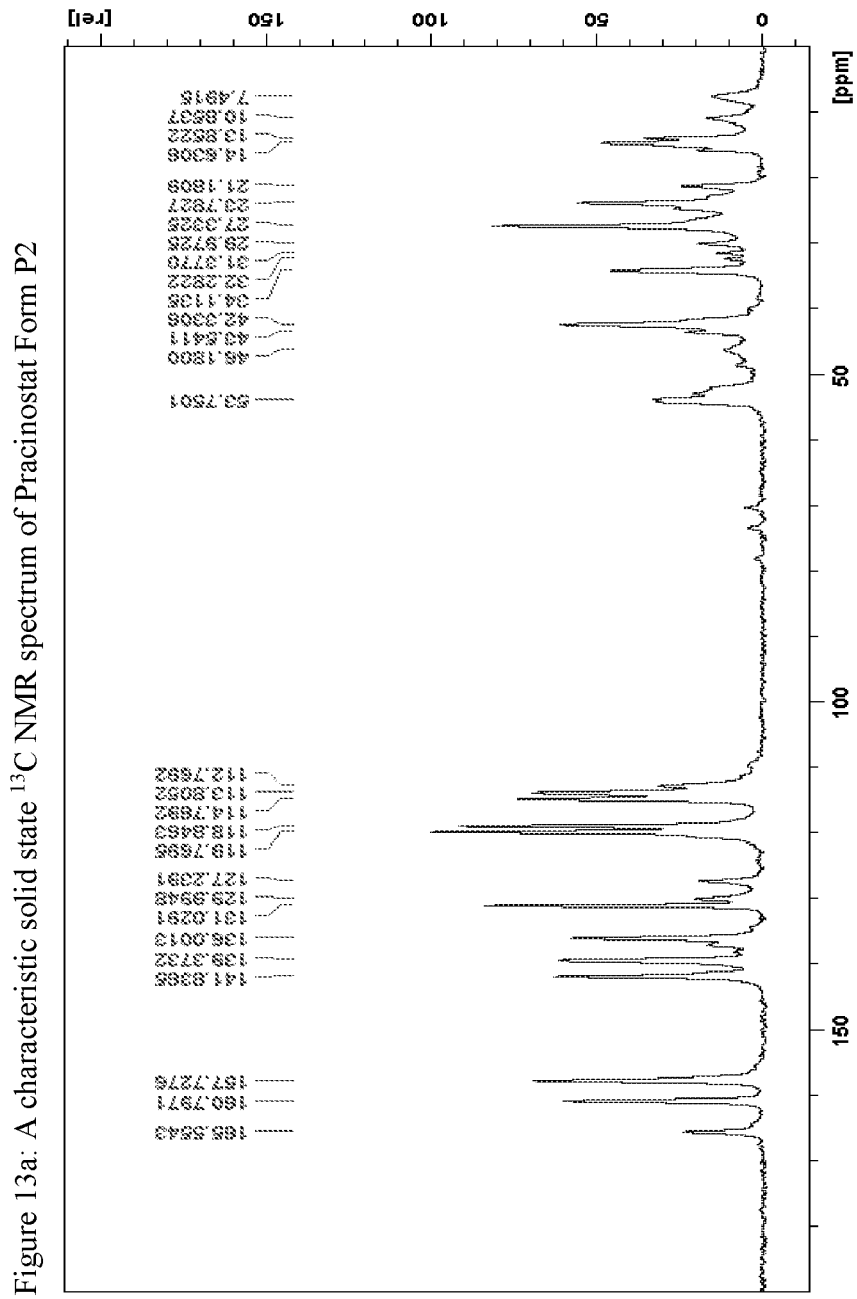
Figure 13a: A characteristic solid state $^{13}$C NMR spectrum of Pracinostat Form P2

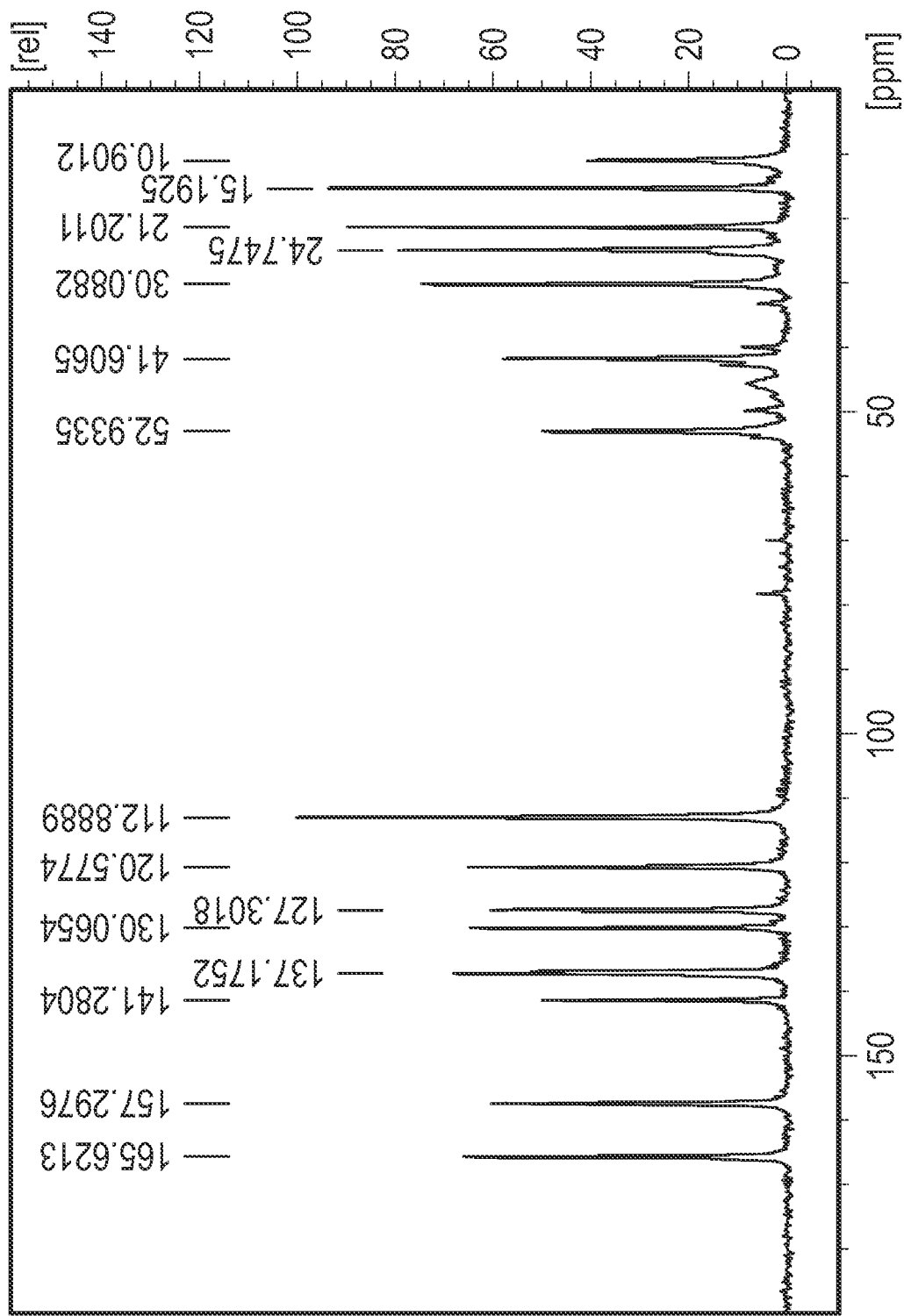

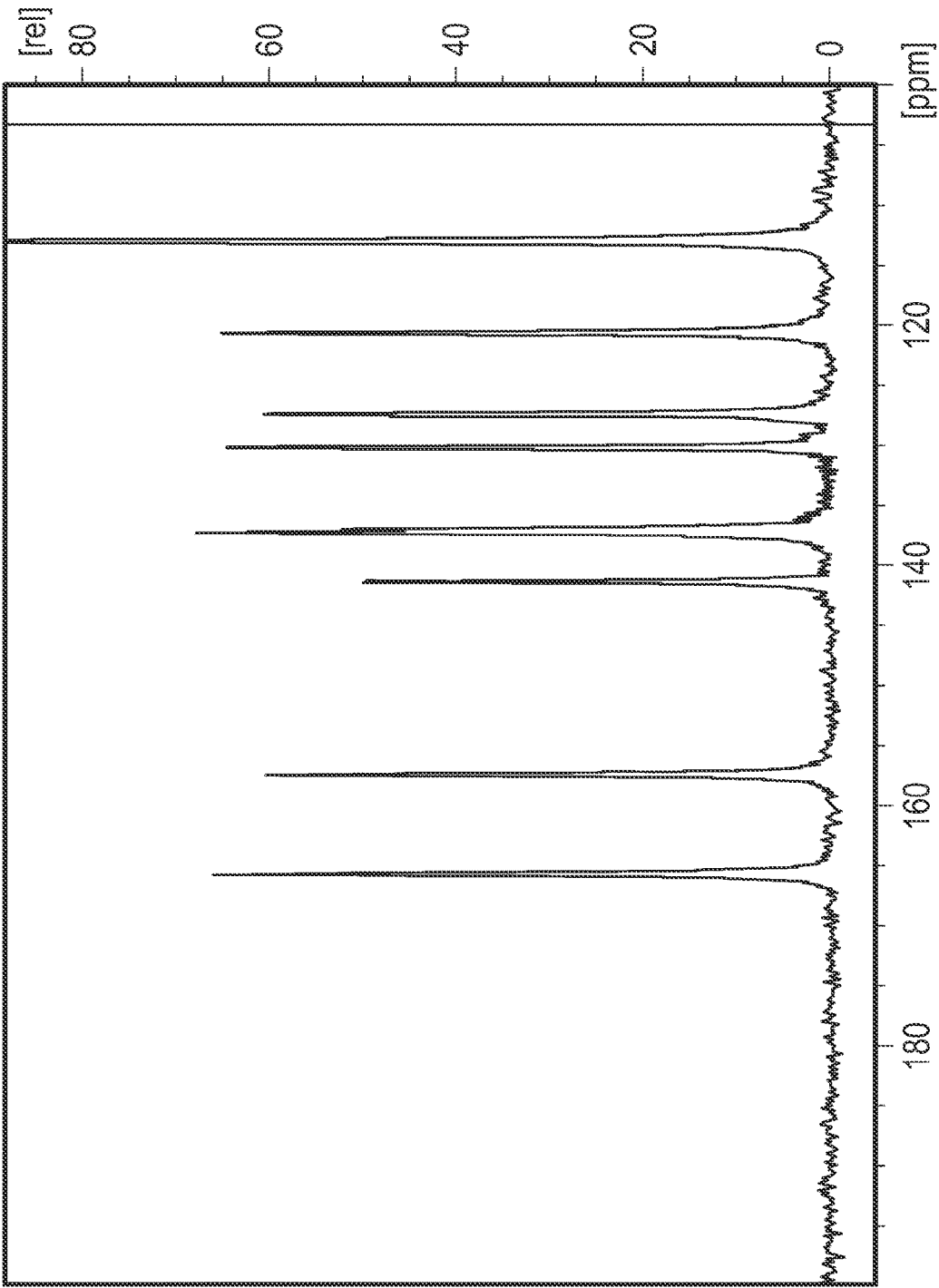

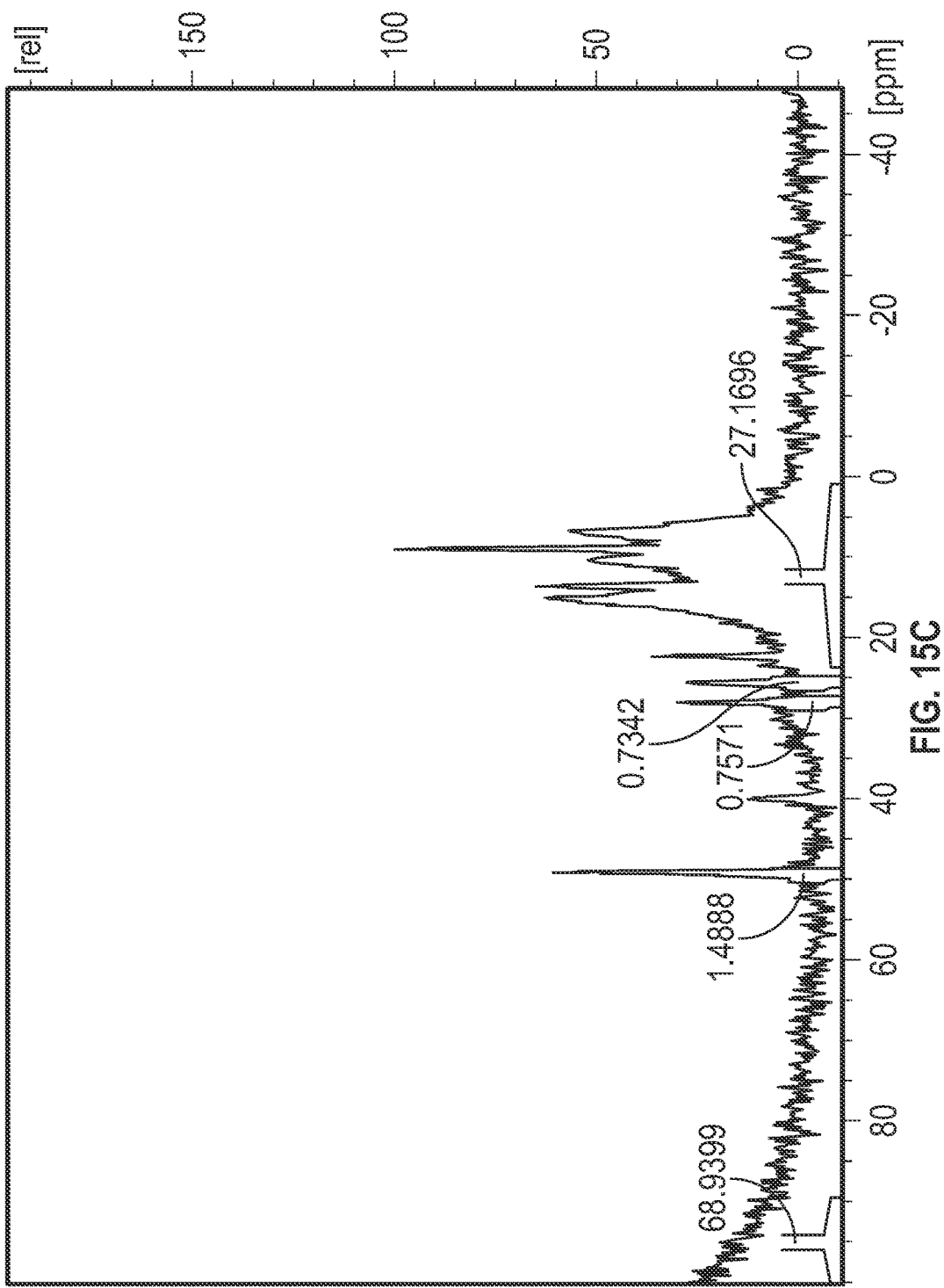

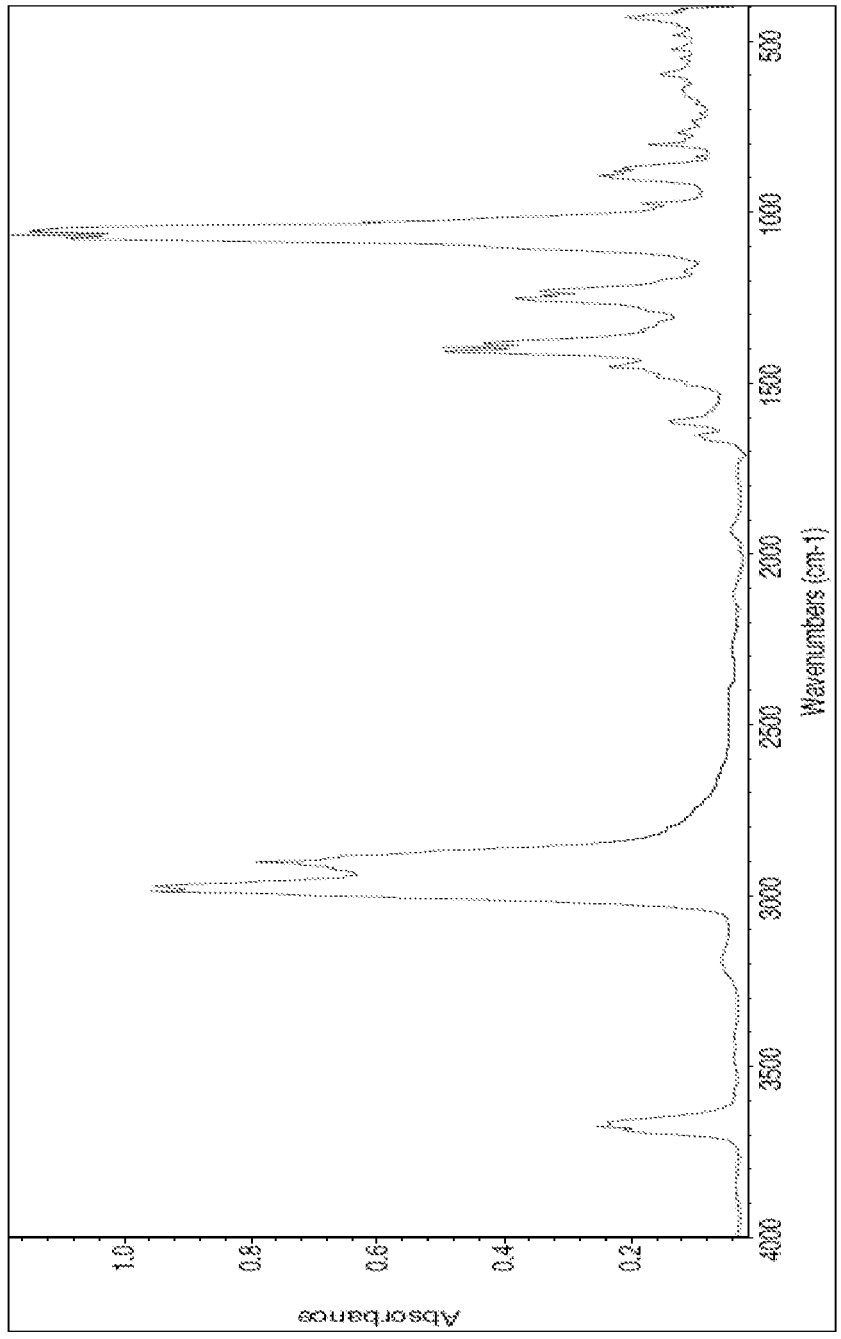
Figure 16: A characteristic FTIR spectrum of Pracinostat Form P2

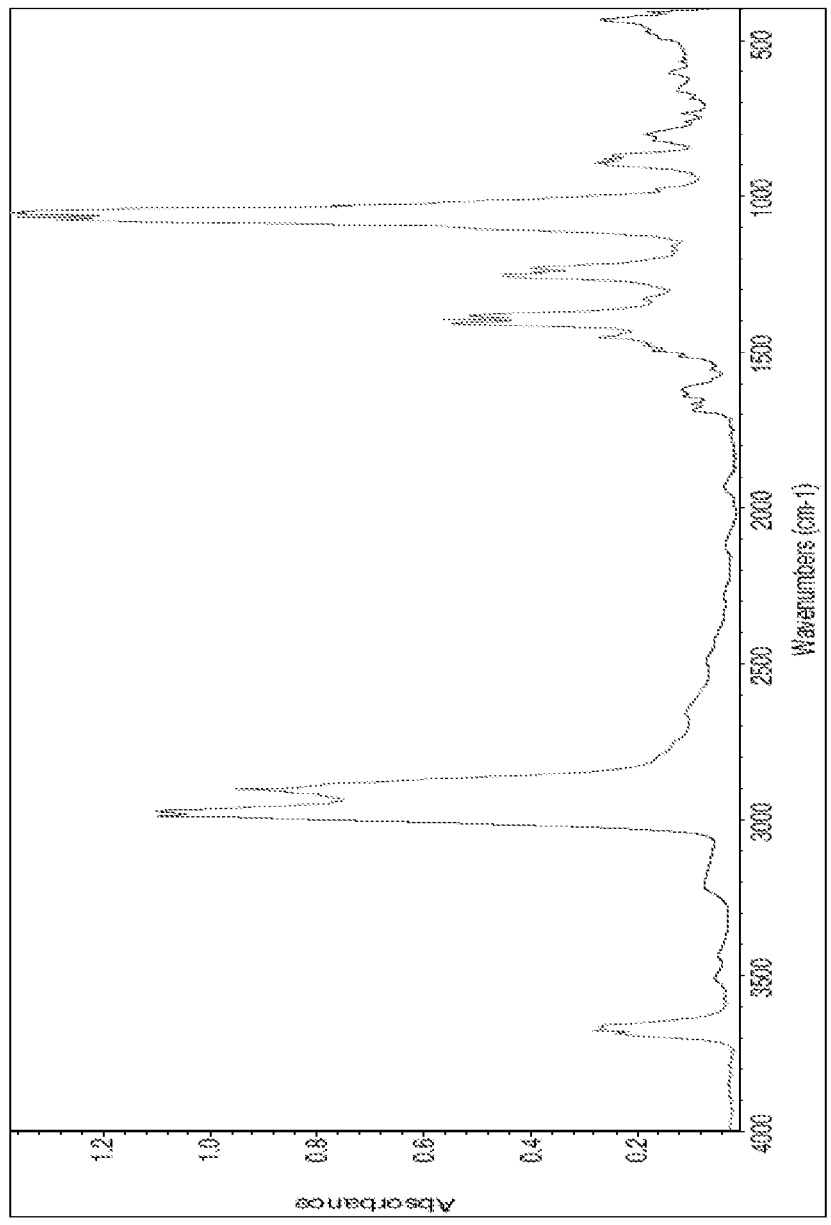
Figure 17: A characteristic FTIR spectrum of Pracinostat Form P3

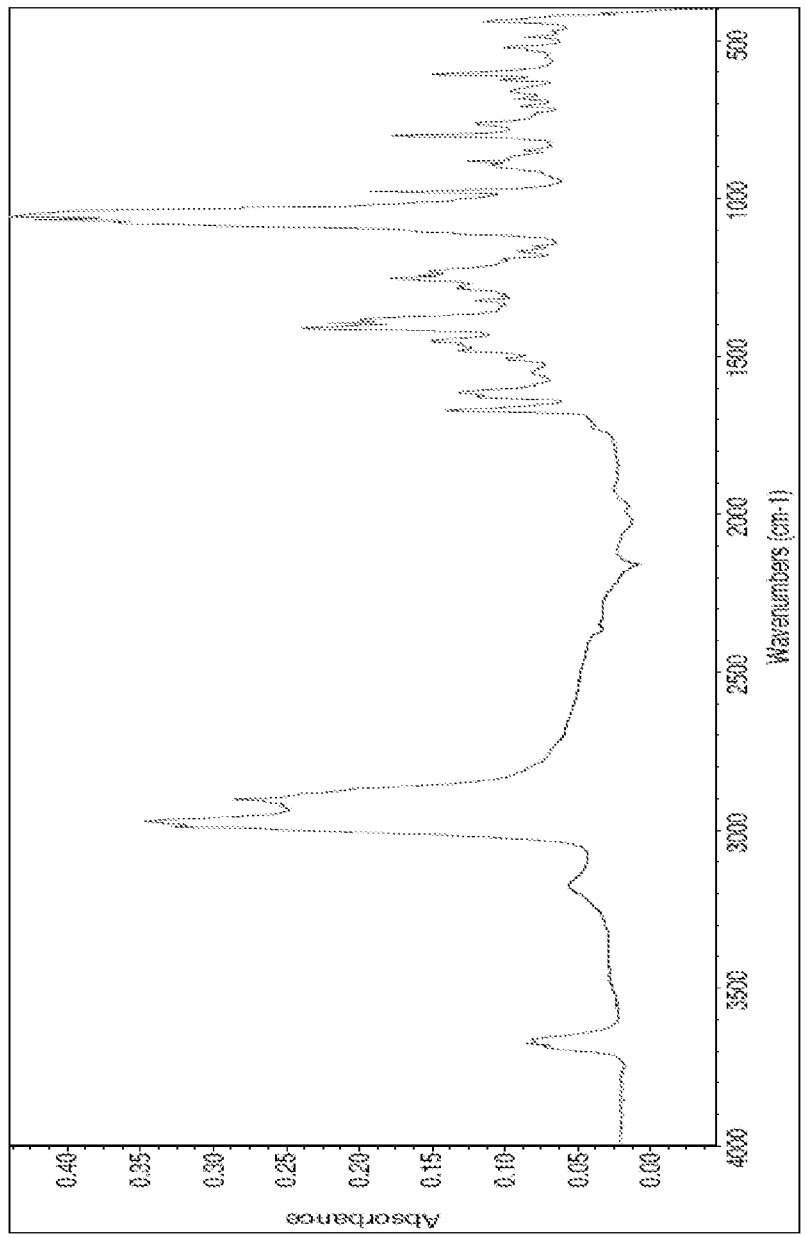
Figure 18: A characteristic FTIR spectrum of Pracinostat Form P4

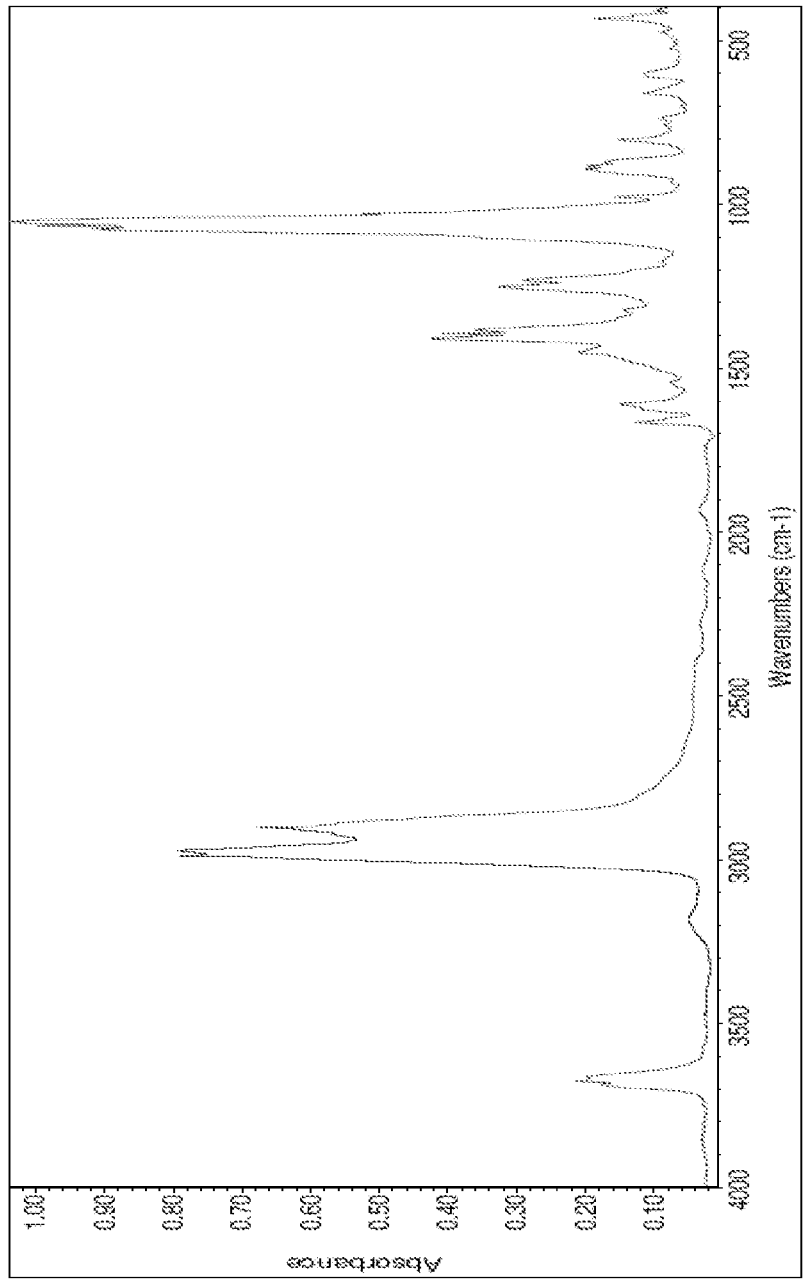
Figure 19: A characteristic FTIR spectrum of Pracinostat Form P6

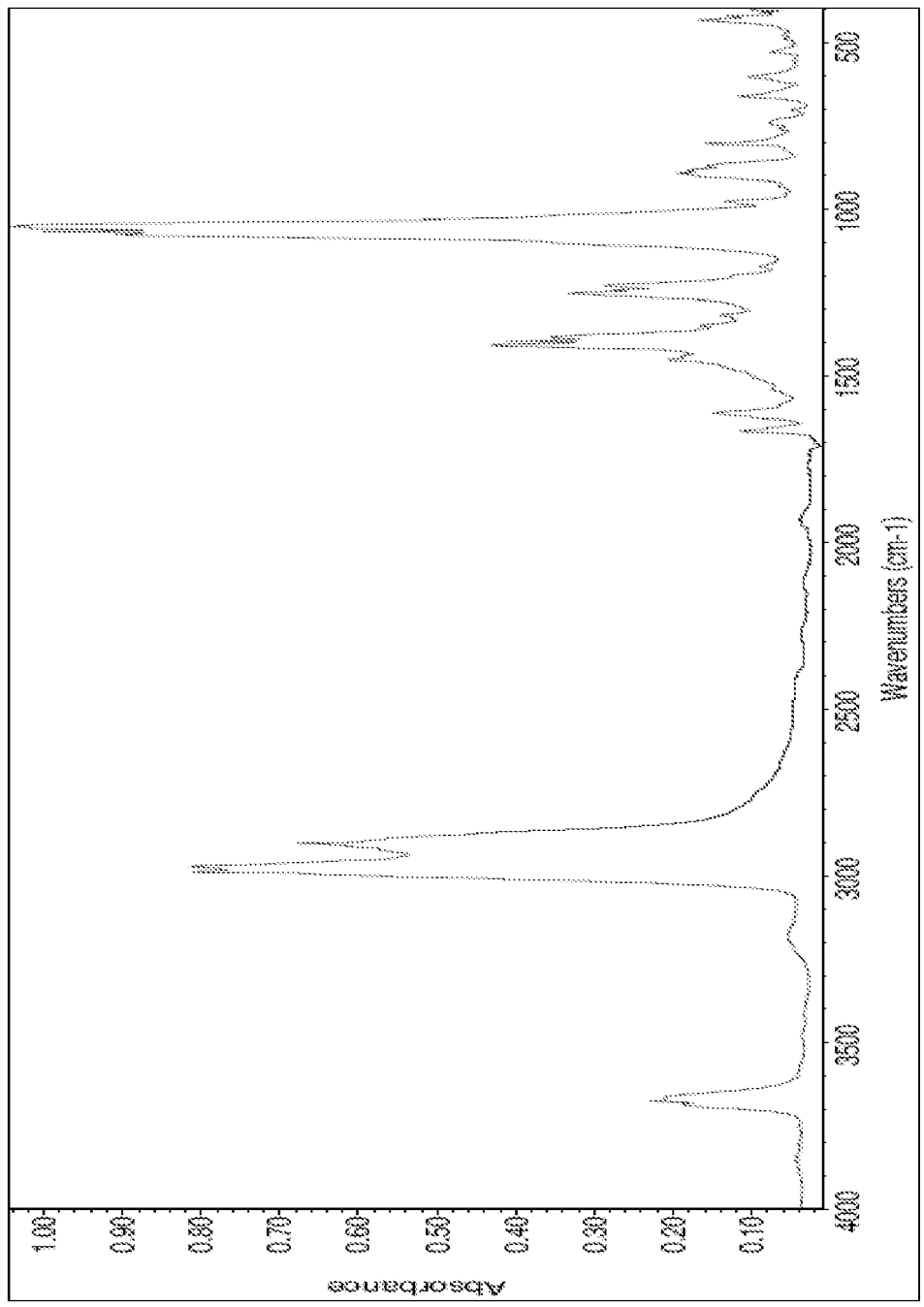
Figure 20: A characteristic FTIR spectrum of Pracinostat Form P7

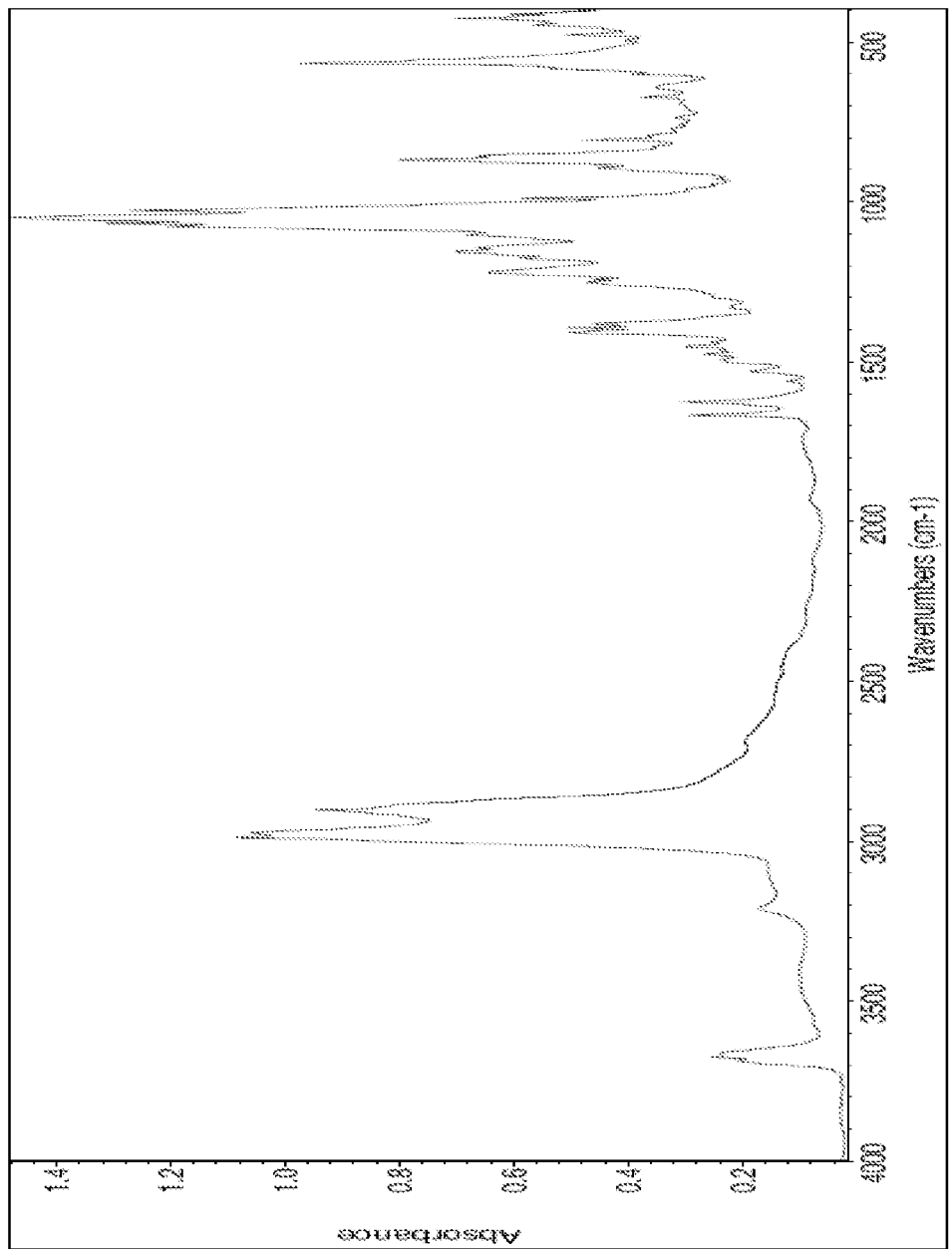
Figure 21: A characteristic FTIR spectrum of Pracinostat sulfate salt Form S1

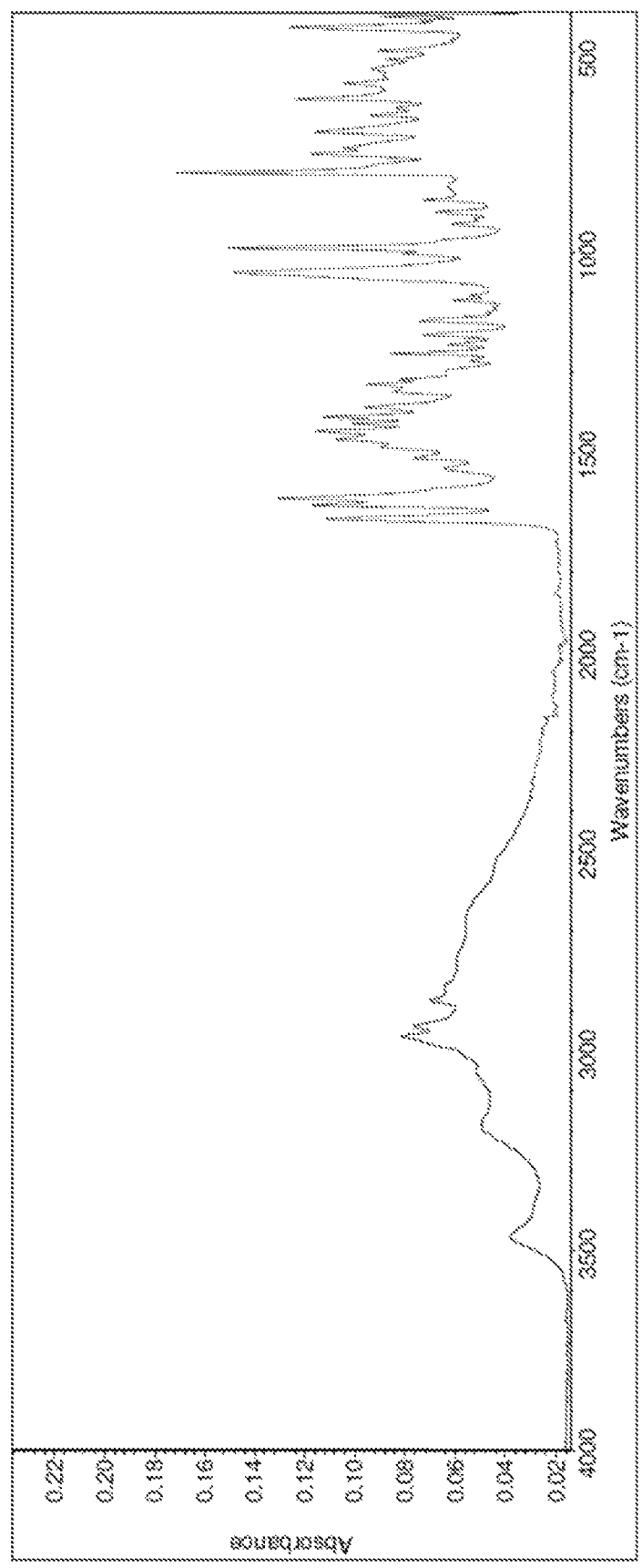
Figure 22: A characteristic FTIR spectrum of Pracinostat Form P1

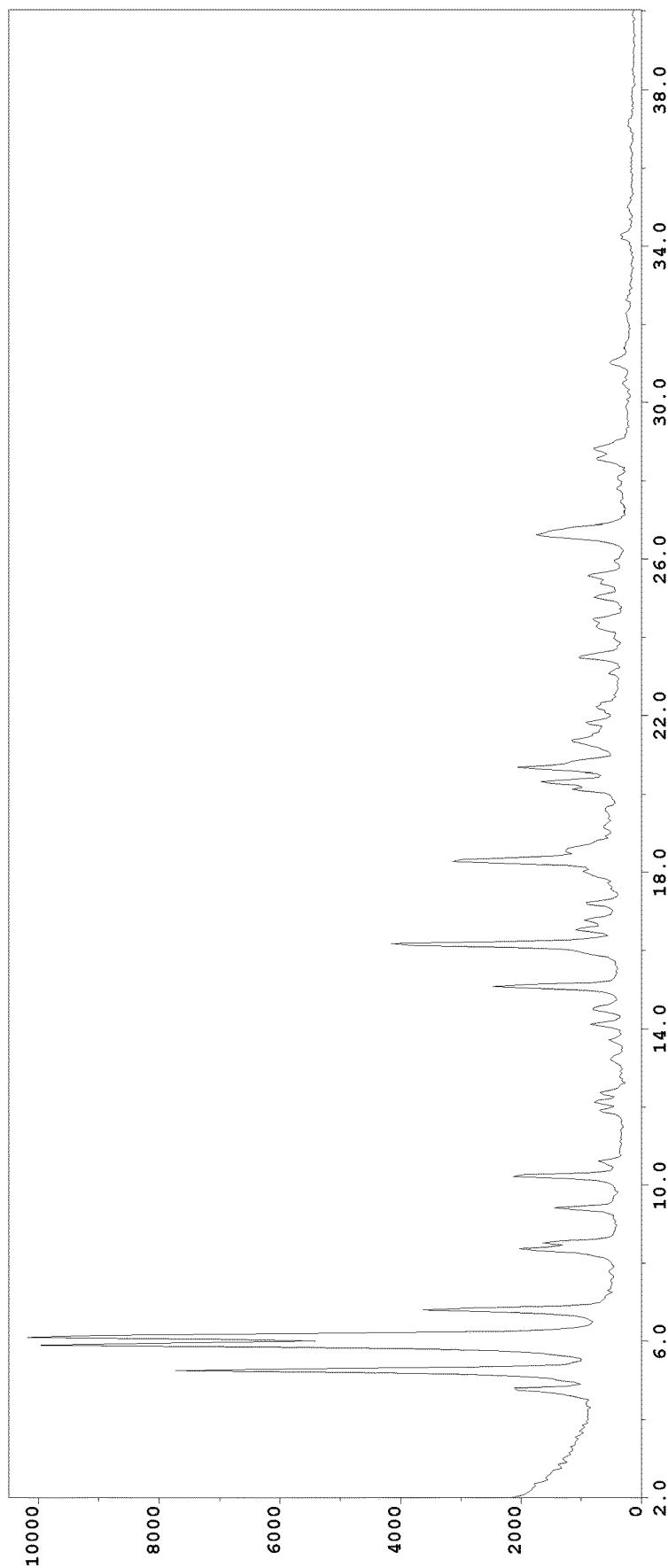
Figure 24: A characteristic X-ray powder diffraction pattern (XRPD) of Pracinostat Form I2 (as butyric acid solvate)

CRYSTALLINE POLYMORPHS OF PRACINOSTAT AND PRACINOSTAT SALTS

CROSS REFERENCE TO RELATED APPLICATIONS

This application is a National Stage Application of, and claims priority to and the benefit of, International Patent Application No. PCT/US2018/066423 filed on Dec. 19, 2018, which, in turn, claims the benefit of, and priority to, U.S. Provisional Application No. 62/607,403 filed Dec. 19, 2017, U.S. Provisional Application No. 62/638,376 filed Mar. 5, 2018, and U.S. Provisional Application No. 62/649,695 filed Mar. 29, 2018, the entire disclosures of each of which are incorporated by reference herein.

FIELD OF THE DISCLOSURE

The present disclosure encompasses crystalline polymorphs of Pracinostat and of Pracinostat salts, and pharmaceutical compositions thereof.

BACKGROUND OF THE DISCLOSURE

Pracinostat's chemical name is (E)-3-[2-Butyl-1-[2-(diethylamino)ethyl]-1H-benzo[d]imidazol-5-yl]-N-hydroxyacrylamide, having the following chemical structure:

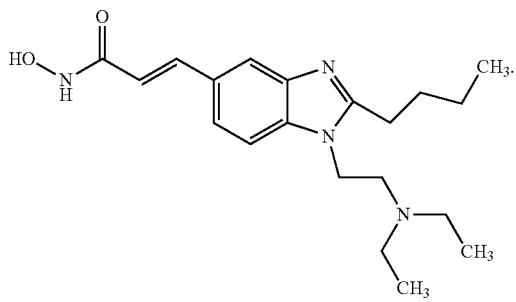 [SMILES: CCCCc1nc2cc(/C=C/C(=O)NO)ccc2n1CCN(CC)CC]

Pracinostat is an oral Histone Deacetylase (HDAC) inhibitor, under development for the treatment of certain pathologies, e.g., acute myeloid leukemia.

The compound is described in PCT publication WO 2007/30080. PCT publication WO 2008/108741 relates to pharmaceutical compositions and use thereof. WO 2017/192451 relates to crystalline forms of Pracinostat Di-HCl. In addition, J. Med. Chem., 2011, 54 (13), pp. 4694-4720, refers, inter alia, to pharmacological and chemical aspects of this molecule.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Pracinostat.

SUMMARY OF THE DISCLOSURE

The present disclosure provides crystalline polymorphs of Pracinostat, and of Pracinostat salts, processes for preparation thereof, and pharmaceutical compositions thereof. These crystalline polymorphs can be used to prepare other forms of Pracinostat or of Pracinostat salts.

The present disclosure provides crystalline polymorphs of Pracinostat and of Pracinostat salts for use in the preparation of pharmaceutical compositions and/or formulations for use in medicine, in embodiments for the treatment of acute myeloid leukemia.

The present disclosure also encompasses the use of crystalline polymorphs of Pracinostat and of Pracinostat salts of the present disclosure for the preparation of pharmaceutical compositions and/or formulations.

In another aspect, the present disclosure provides pharmaceutical compositions including any one or a combination of the crystalline polymorphs of Pracinostat and/or of Pracinostat salts according to the present disclosure.

In yet another embodiment, the present disclosure encompasses pharmaceutical formulations including any one or a combination of the described crystalline polymorphs of Pracinostat and/or of Pracinostat salts, or pharmaceutical compositions including any one or a combination of the described crystalline polymorph of Pracinostat and/or of Pracinostat salts and at least one pharmaceutically acceptable excipient.

The present disclosure includes processes for preparing the above-mentioned pharmaceutical compositions. The processes include combining any one or a combination of crystalline polymorph of Pracinostat and/or of Pracinostat salts with at least one pharmaceutically acceptable excipient.

The crystalline polymorphs of Pracinostat and of Pracinostat salts as defined herein and the pharmaceutical compositions or formulations of the crystalline polymorphs of Pracinostat and of Pracinostat salts may be used as medicaments, in embodiments for the treatment of acute myeloid leukemia.

The present disclosure also provides methods of treating acute myeloid leukemia, including administering a therapeutically effective amount of any one or a combination of crystalline polymorphs of Pracinostat and/or of Pracinostat salts of the present disclosure, or at least one of the above pharmaceutical compositions or formulations, to a subject suffering from acute myeloid leukemia, or otherwise in need of the treatment.

The present disclosure also provides the uses of crystalline polymorphs of Pracinostat and of Pracinostat salts of the present disclosure, or at least one of the above pharmaceutical compositions or formulations, for the manufacture of medicaments.

BRIEF DESCRIPTION OF THE DRAWINGS

FIG. 13a shows characteristic solid state $^{13}$C NMR spectrum of Pracinostat Form P2.

FIG. 14a shows characteristic solid state $^{13}$C NMR spectrum of Pracinostat Form P3.

FIG. 14b shows characteristic solid state $^{13}$C NMR spectrum of Pracinostat Form P3 (at the range 100-200 ppm).

FIG. 15c shows characteristic solid state $^{13}$C NMR of Pracinostat sulfate salt Form S1 (at the range 0-100 ppm).

FIG. 16 shows characteristic FTIR spectrum of Pracinostat Form P2.

FIG. 17 shows characteristic FTIR spectrum of Pracinostat Form P3.

FIG. 18 shows characteristic FTIR spectrum of Pracinostat Form P4.

FIG. 19 shows characteristic FTIR spectrum of Pracinostat Form P6.

FIG. 20 shows characteristic FTIR spectrum of Pracinostat Form P7.

FIG. 21 shows characteristic FTIR spectrum of Pracinostat sulfate salt Form S1.

FIG. 22 shows characteristic FTIR spectrum of Pracinostat Form P1.

FIG. 24 shows characteristic X-ray powder diffraction pattern (XRPD) of Pracinostat Form I2 (as butyric acid solvate).

DETAILED DESCRIPTION OF THE DISCLOSURE

Figure 1:
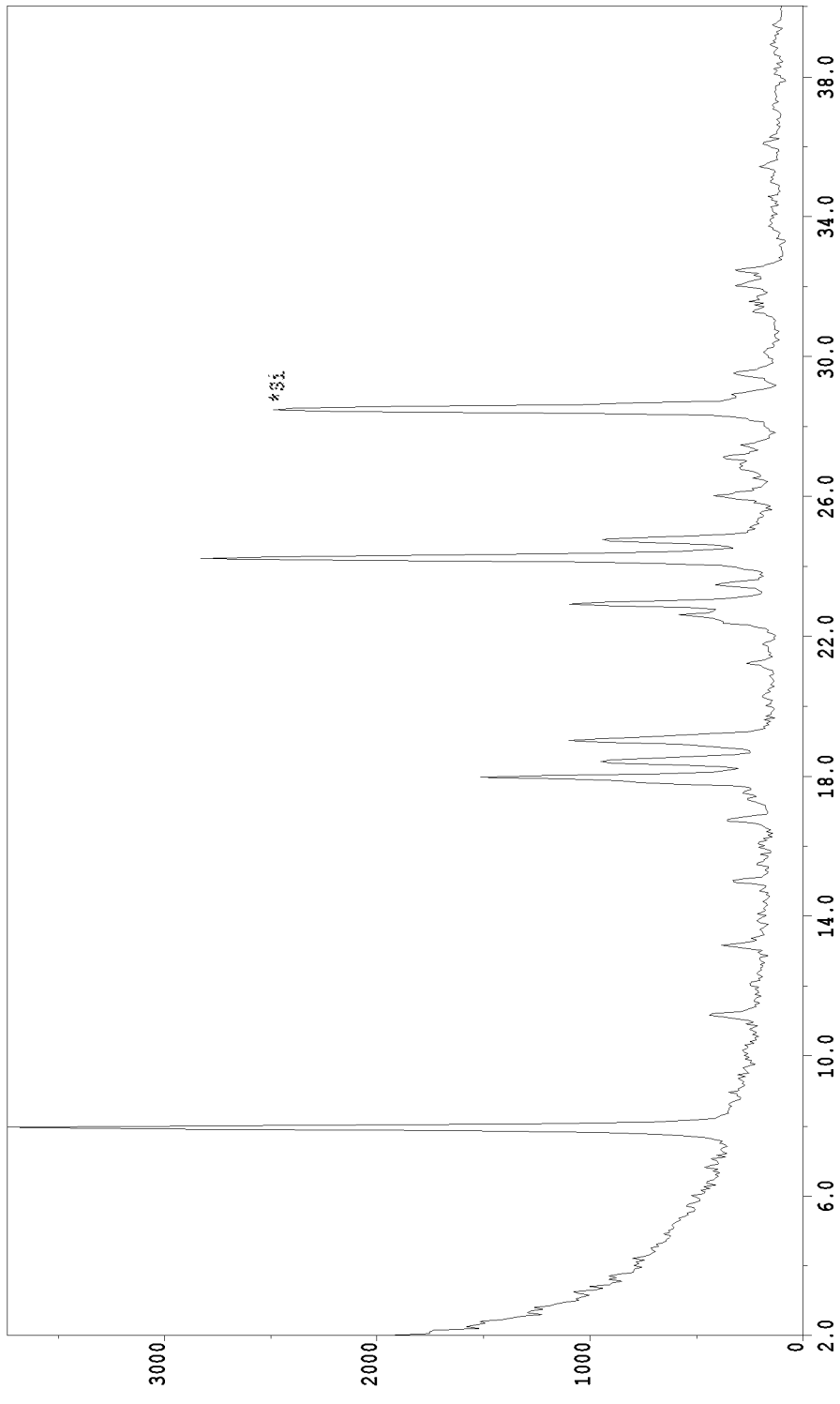
FIG. 1 shows a characteristic X-ray powder diffraction pattern (XRPD) of Pracinostat Form P1.

The present disclosure encompasses crystalline polymorphs of Pracinostat and of Pracinostat salts. Solid state properties of Pracinostat and Pracinostat salts and crystalline polymorphs thereof can be influenced by controlling the conditions under which Pracinostat and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Pracinostat described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Pracinostat. In some embodiments of the disclosure, the described crystalline polymorph of Pracinostat may contain from about 1% to about 20% (w/w), from about 5% to about 20% (w/w), or from about 5% to about 10% (w/w) of one or more other crystalline polymorph of the same Pracinostat.

Depending on other crystalline polymorphs to which a comparison is made, the crystalline polymorphs of Pracinostat of the present disclosure has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid-state NMR spectra. As is well known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Pracinostat referred to herein as being characterized by graphical data "as depicted in" or "as substantially depicted in" a Figure will thus be understood to include any crystal forms of Pracinostat characterized with the graphical data having such small variations, as are well known to the skilled person, in comparison with the Figure.

As used herein the term non-hygroscopic in relation to crystalline forms of Pracinostat refers to less than 0.2% (w/w) absorption of water, by the crystalline form of Pracinostat, as determined for example by TGA. Water can be for example atmospheric water.

As used herein, and unless stated otherwise, the term "anhydrous" in relation to crystalline forms of Pracinostat, relates to a crystalline form of Pracinostat that does not include any crystalline water (or other solvents) in a defined, stoichiometric amount within the crystal. Moreover, an "anhydrous" form would typically not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the term "isolated" in reference to crystalline polymorph of Pracinostat of the present disclosure corresponds to a crystalline polymorph of Pracinostat that is physically separated from the reaction mixture in which it is formed.

As used herein, unless stated otherwise, the XRPD measurements are taken using copper Kα radiation wavelength 1.54184 Å. XRPD peaks reported herein are measured using CuK α radiation, λ=1.5418 Å, at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A processor step may be referred to herein as being carried out "overnight." This refers to a time interval, e.g., for the process or step, that spans the time during the night, when that process or step may not be actively observed. This time interval is from about 8 to about 20 hours, or about 10-18 hours, in embodiments about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Pracinostat, designated Form P1. The crystalline Form P1 of Pracinostat may be characterized by data selected from one or more of the following: an X-ray powder diffraction pattern substantially as depicted in FIG. 1; an X-ray powder diffraction pattern having peaks at 7.9, 11.1, 13.1, 15.0 and 16.7 degrees 2-theta±0.2 degrees 2-theta; a FTIR spectrum substantially as depicted in FIG. 22; and combinations of these data.

Crystalline Form P1 of Pracinostat may be further characterized by an X-ray powder diffraction pattern having peaks at 7.9, 11.1, 13.1, 15.0 and 16.7 degrees 2-theta±0.2 degrees 2-theta, and also having any one, two, three, four or five additional peaks selected from 10.0, 17.9, 18.4, 22.7 and 24.2 degrees 2-theta±0.2 degrees 2-theta.

Crystalline Form P1 of Pracinostat may possess water content of from about 4.30 to about 6.20, in embodiments about 4.68% as measured by KF. Accordingly, Form P1 may be a monohydrate.

Crystalline Form P1 of Pracinostat may be characterized by each of the above characteristics alone or by all possible combinations, e.g., an XRPD pattern having peaks at 7.9, 11.1, 13.1, 15.0 and 16.7 degrees 2-theta±0.2 degrees 2-theta; an XRPD pattern as depicted in FIG. 1, and combinations thereof.

In one embodiment of the present disclosure, crystalline Form P1 of Pracinostat is isolated.

Figure 13B:
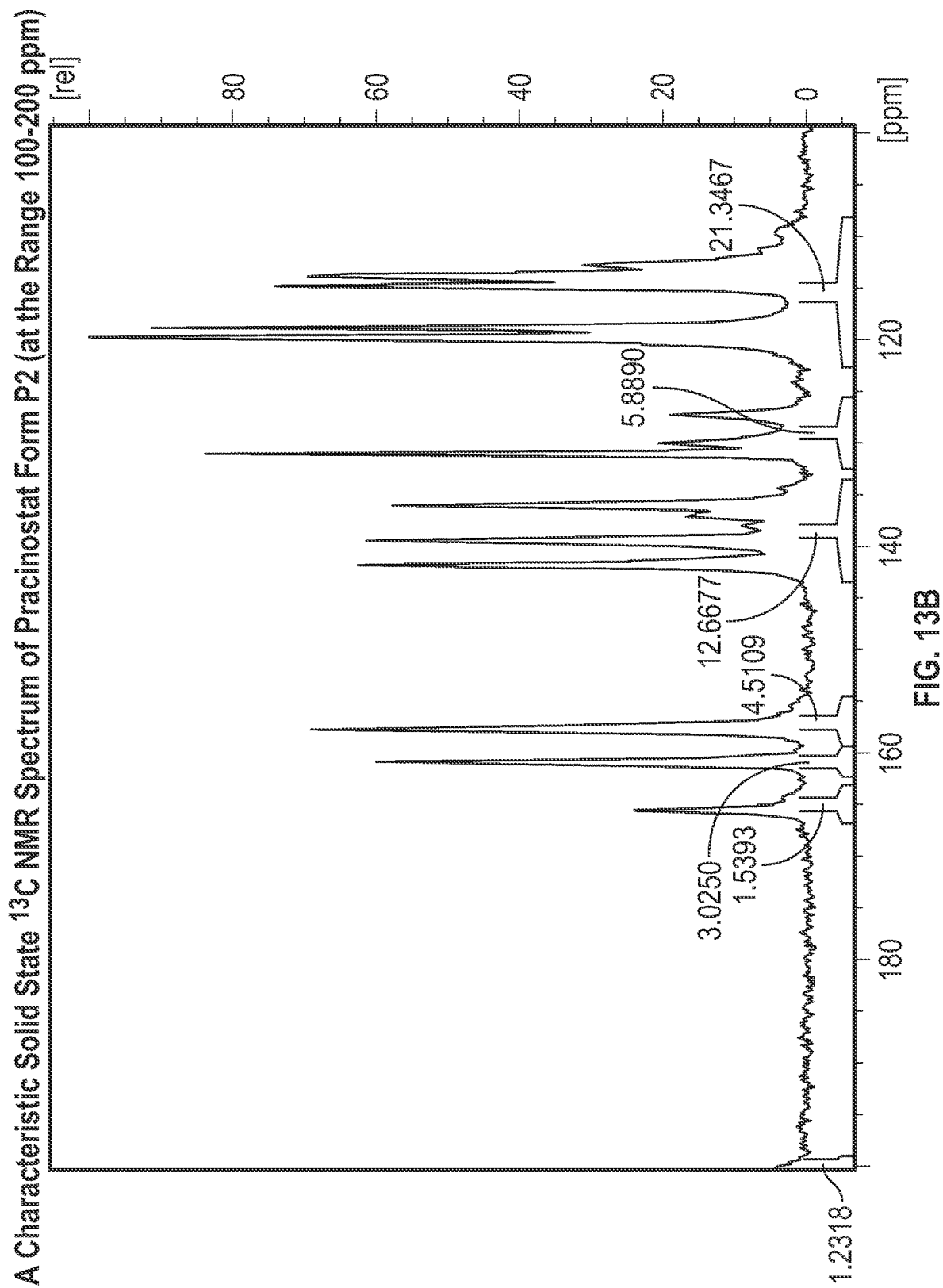
FIG. 13b shows characteristic solid state $^{13}$C NMR spectrum of Pracinostat Form P2 (at the range 100-200 ppm).
Figure 13C:
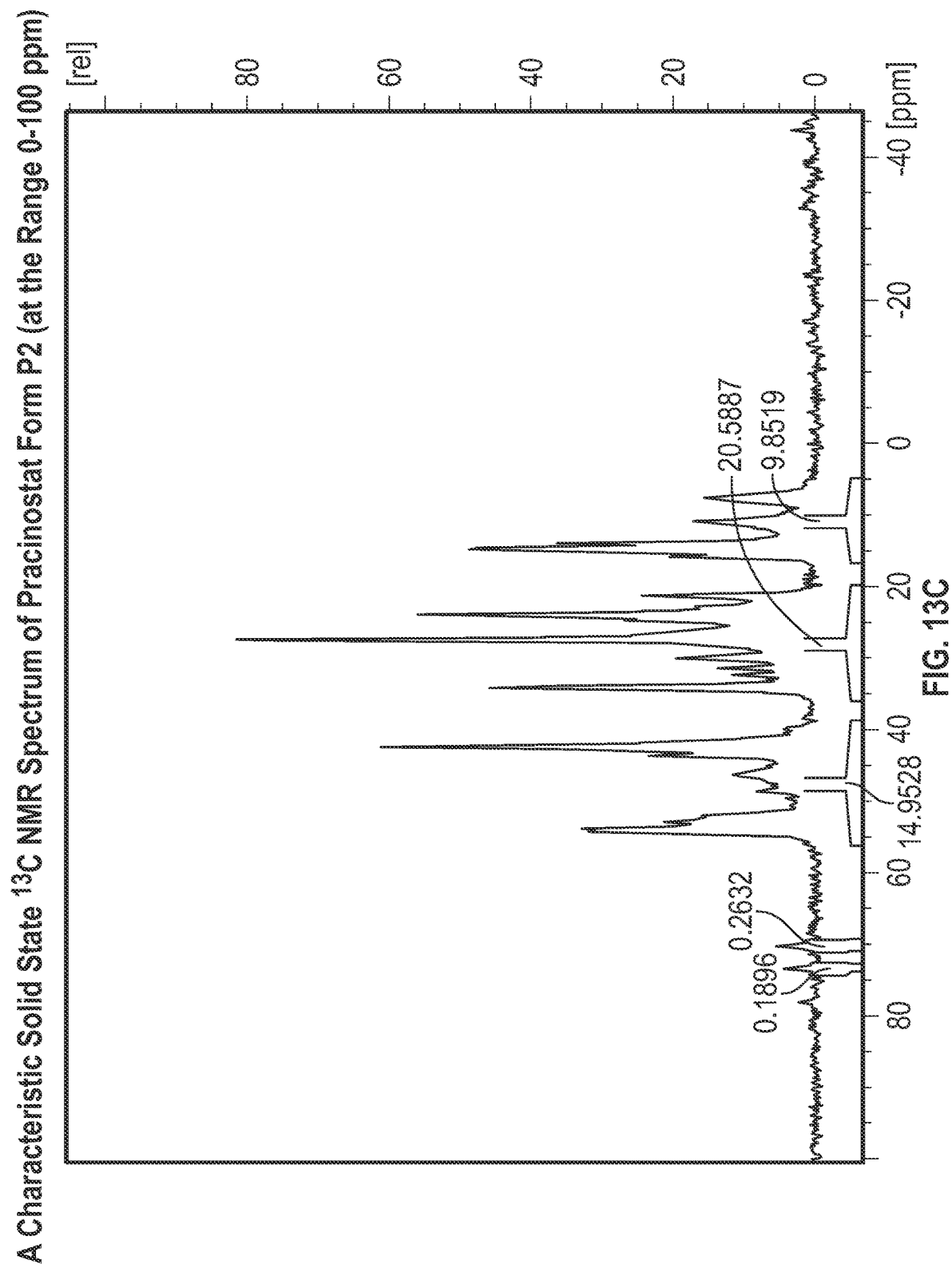
FIG. 13c shows characteristic solid state $^{13}$C NMR spectrum of Pracinostat Form P2 (at the range 0-100 ppm).

The present disclosure further includes, a crystalline polymorph of Pracinostat, designated Form P2. The crystalline Form P2 of Pracinostat may be characterized by data selected from one or more of the following: an X-ray powder diffraction pattern substantially as depicted in FIG. 2; an X-ray powder diffraction pattern having peaks at 4.3, 4.6, 8.7, 9.5 and 12.3 degrees 2-theta±0.2 degrees 2-theta; a solid state $^{13}$C NMR spectrum substantially as depicted in any one of FIGS. 13a, 13b and 13c; a solid state $^{13}$C NMR spectrum having peaks at the range of 100-200 ppm at 160.79, 139.37, 131.03, 118.84 and 114.76 ppm±2 ppm; a solid state $^{13}$C NMR spectrum having the following chemical shift absolute differences from a peak at 165.55 ppm±2 ppm of 4.79, 26.18, 34.52, 46.71 and 50.79 ppm±2 ppm; a solid state $^{13}$C NMR spectrum having chemical shift difference from a peak at 165.55 ppm±1 ppm to 131.03 ppm±1 ppm of 34.52 ppm±1 ppm; a FTIR spectrum substantially as depicted in FIG. 16; and combinations of these data.

Crystalline Form P2 of Pracinostat may be further characterized by an X-ray powder diffraction pattern having peaks at 4.3, 4.6, 8.7, 9.5 and 12.3 degrees 2-theta±0.2 degrees 2-theta, and also having any one, two, three, four or five additional peaks selected from 19.1, 20.1, 20.7, 21.2 and 24.1 degrees 2-theta±0.2 degrees 2-theta.

Crystalline Form P2 of Pracinostat may be a methanol solvate.

Figure 2:
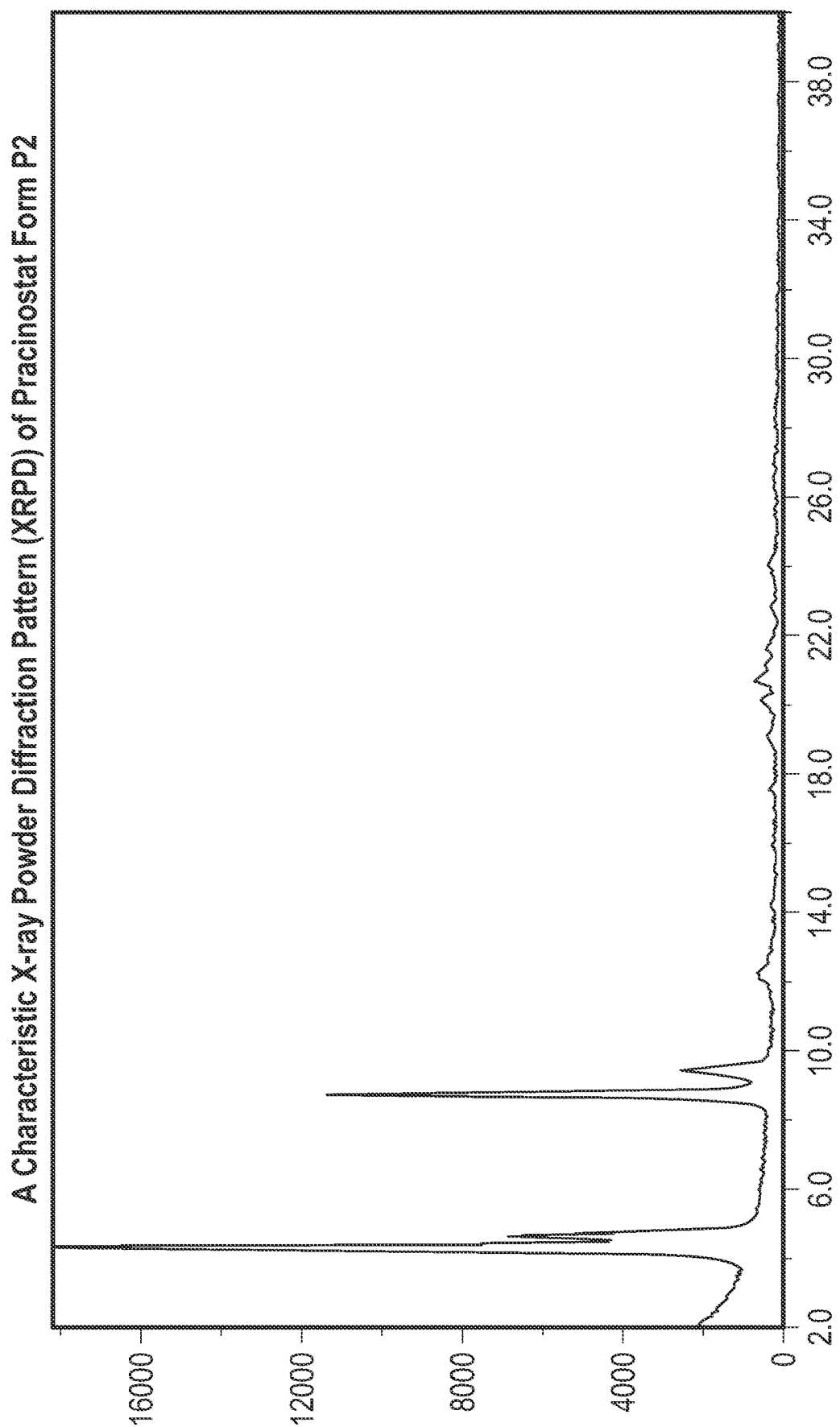
FIG. 2 shows a characteristic X-ray powder diffraction pattern (XRPD) of Pracinostat Form P2.

Crystalline Form P2 of Pracinostat may be characterized by each of the above characteristics alone or by all possible combinations, e.g., an XRPD pattern having peaks at 4.3, 4.6, 8.7, 9.5 and 12.3 degrees 2-theta±0.2 degrees 2-theta; an XRPD pattern as depicted in FIG. 2, and combinations thereof.

In one embodiment of the present disclosure, crystalline Form P2 of Pracinostat is isolated.

Figure 14C:
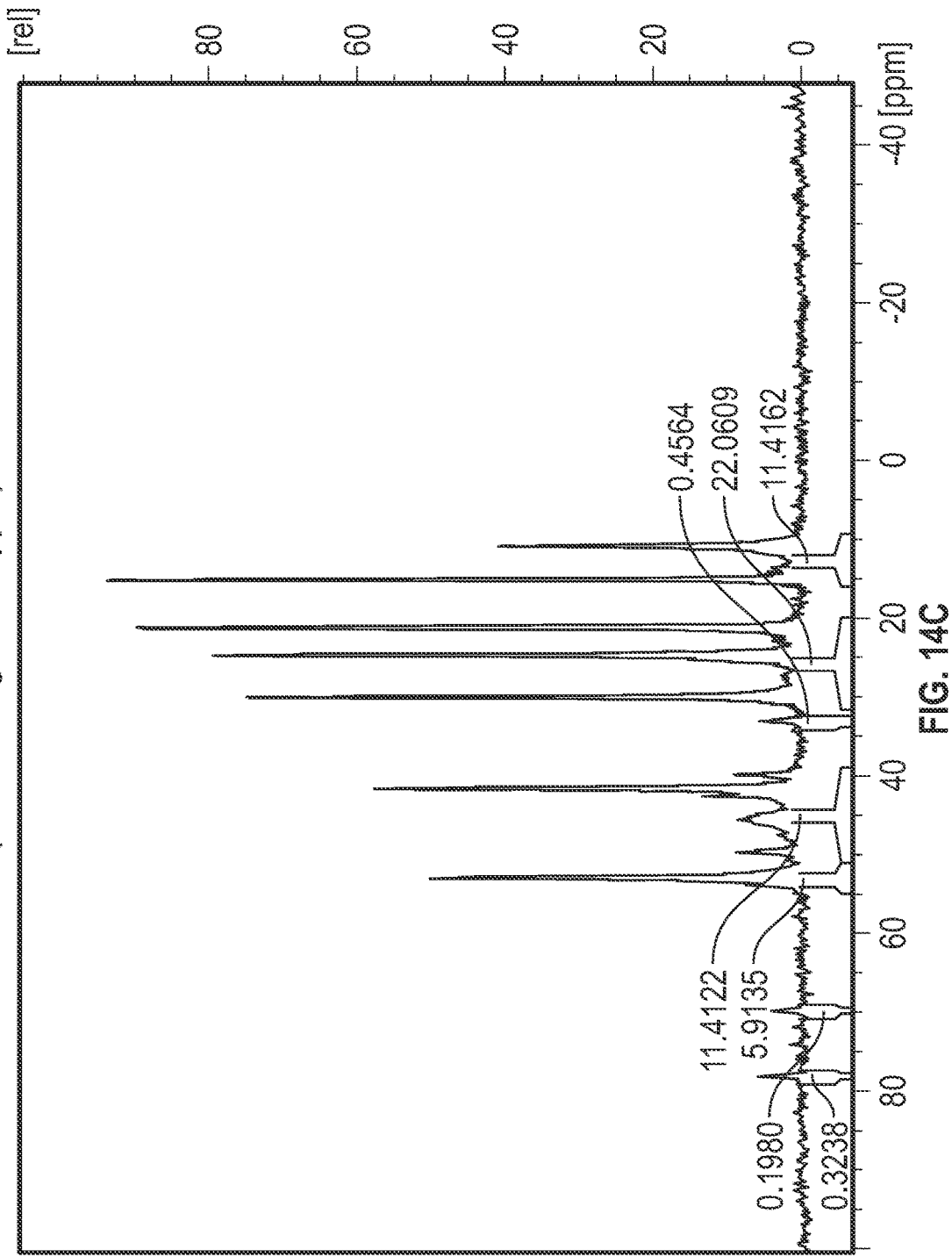
FIG. 14c shows characteristic solid state $^{13}$C NMR of Pracinostat Form P3 (at the range 0-100 ppm).

The present disclosure further includes a crystalline polymorph of Pracinostat, designated Form P3. The crystalline Form P3 of Pracinostat may be characterized by data selected from one or more of the following: an X-ray powder diffraction pattern substantially as depicted in FIG. 3; an X-ray powder diffraction pattern having peaks at 5.7, 8.4, 10.2, 14.3 and 15.3 degrees 2-theta±0.2 degrees 2-theta; a solid state $^{13}$C NMR spectrum substantially as depicted in any one of FIGS. 14a, 14b and 14c; a solid state $^{13}$C NMR spectrum having peaks at the range of 100-200 ppm at 157.29, 141.28, 137.17, 130.06 and 120.57 ppm±2 ppm; a solid state $^{13}$C NMR spectrum having the following chemical shift absolute differences from a peak at 165.62 ppm±2 ppm of 8.33, 24.34, 28.45, 35.56 and 45.05±2 ppm; a solid state $^{13}$C NMR spectrum having chemical shift difference from a peak at 165.62 ppm±1 ppm to 130.06 ppm±1 ppm of 35.36 ppm±1 ppm; a FTIR spectrum substantially as depicted in FIG. 17; and combinations of these data.

Crystalline Form P3 of Pracinostat may be further characterized by an X-ray powder diffraction pattern having peaks at 5.7, 8.4, 10.2, 14.3 and 15.3 degrees 2-theta±0.2 degrees 2-theta, and also having any one, two, three, four or five additional peaks selected from 16.5, 17.8, 20.1, 20.9 and 23.3 degrees 2-theta±0.2 degrees 2-theta.

Crystalline Form P3 of Pracinostat may be an anhydrous form.

Figure 3:
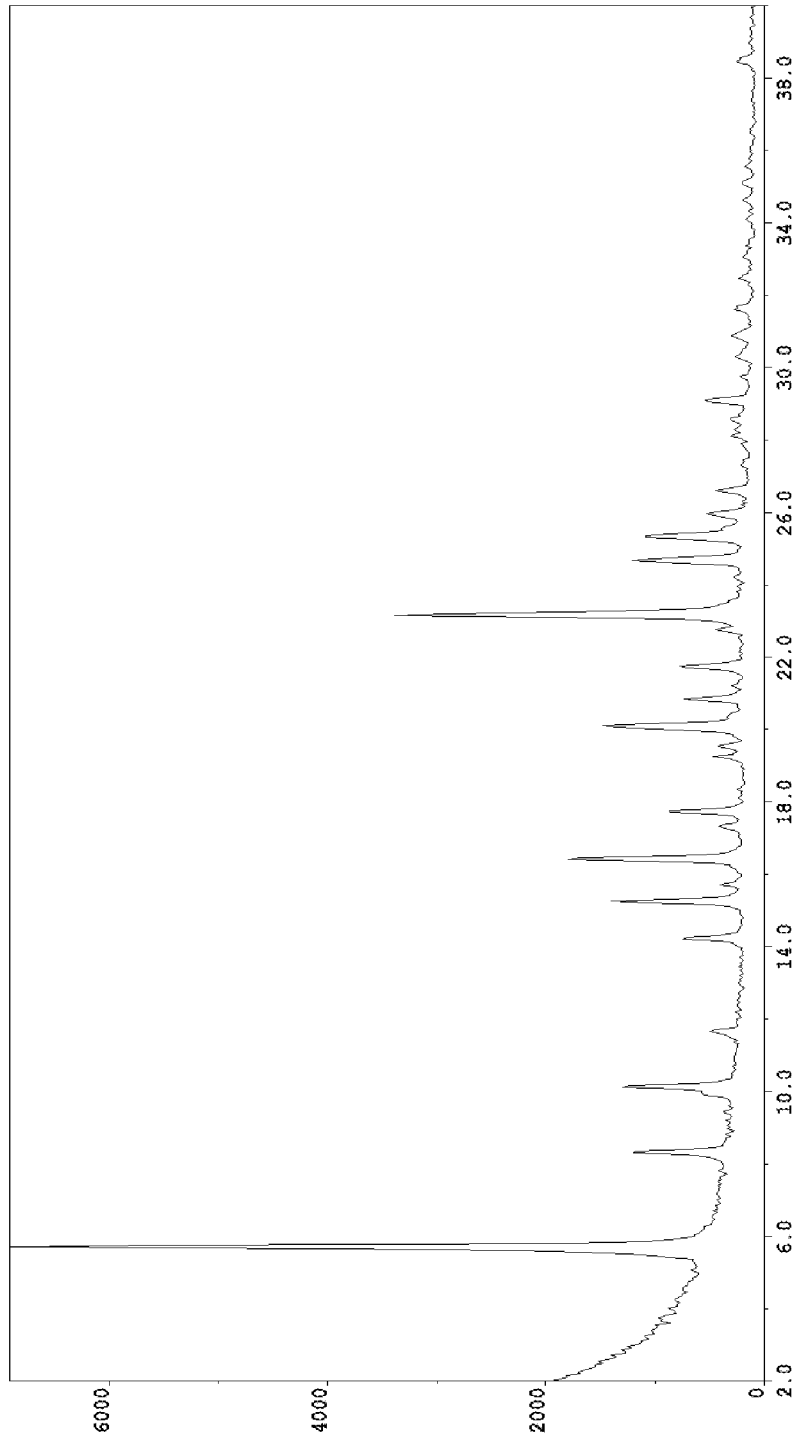
FIG. 3 shows a characteristic X-ray powder diffraction pattern (XRPD) of Pracinostat Form P3.

Crystalline Form P3 of Pracinostat may be characterized by each of the above characteristics alone or by all possible combinations, e.g., an XRPD pattern having peaks at 5.7, 8.4, 10.2, 14.3 and 15.3 degrees 2-theta±0.2 degrees 2-theta; an XRPD pattern as depicted in FIG. 3, and combinations thereof.

In one embodiment of the present disclosure, crystalline Form P3 of Pracinostat is isolated.

Crystalline Form P3 of Pracinostat may have any one of the above-described advantageous properties. For example, Form P3 is stable under grinding, physical pressure and thermal tests. In addition, it is non-hygroscopic, i.e., it absorbs water to the extent of less than 0.2% (w/w) and it is polymorphically stable at relative humidity ("RH") of from 0% to 100%, for a period of at least 7 days, at room temperature.

The present disclosure further includes a crystalline polymorph of Pracinostat, designated Form P4. The crystalline Form P4 of Pracinostat may be characterized by data selected from one or more of the following: an X-ray powder diffraction pattern substantially as depicted in FIG. 4; an X-ray powder diffraction pattern having peaks at 5.4, 10.8, 15.8, 21.8 and 25.6 degrees 2-theta±0.2 degrees 2-theta; a FTIR spectrum substantially as depicted in FIG. 18; and combinations of these data.

Crystalline Form P4 of Pracinostat may be further characterized by an X-ray powder diffraction pattern having peaks at 5.4, 10.8, 15.8, 21.8 and 25.6 degrees 2-theta±0.2 degrees 2-theta, and also having any one, two, three, four or five additional peaks selected from 14.9, 16.3, 16.9, 18.7 and 19.3 degrees 2-theta±0.2 degrees 2-theta.

Figure 4:
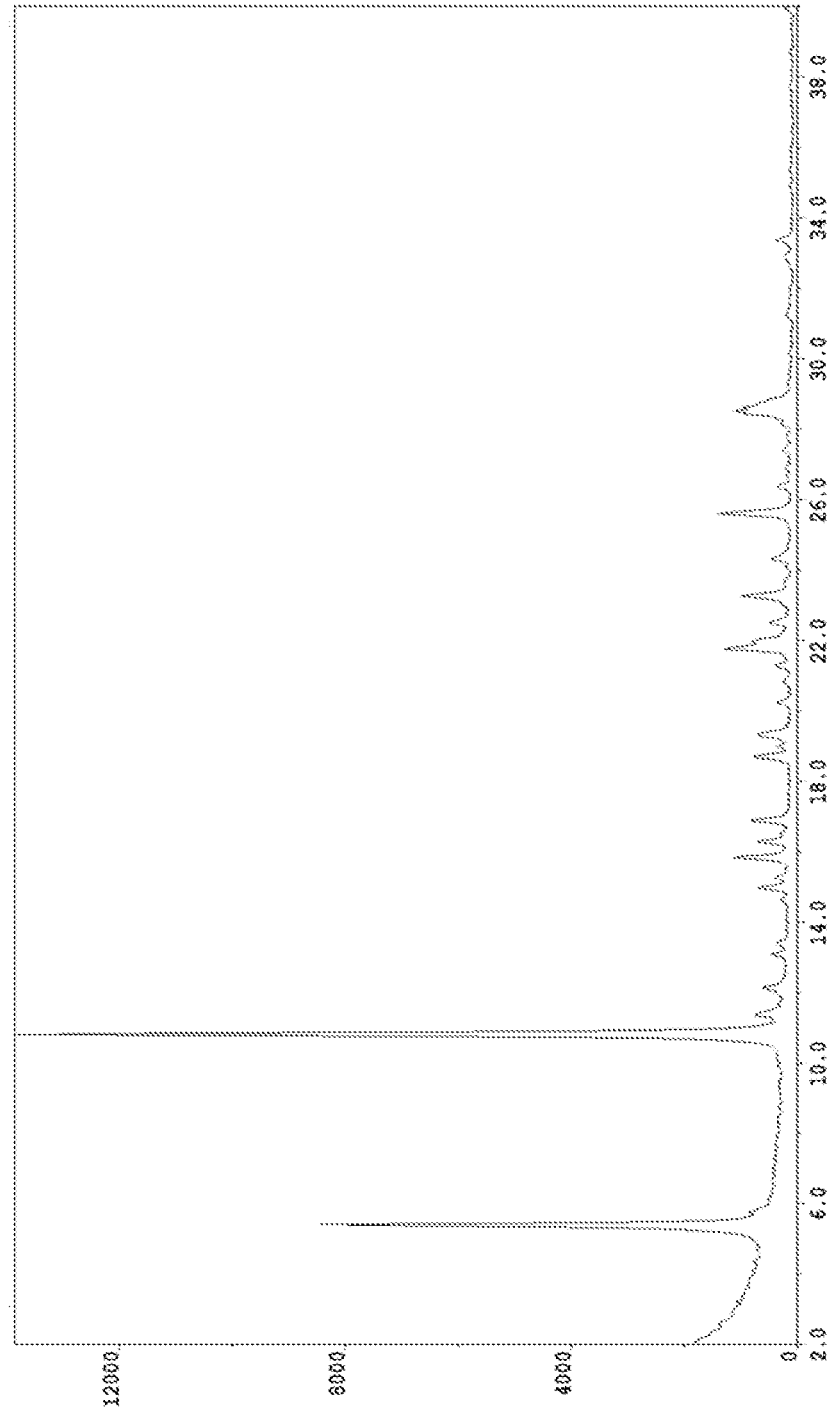
FIG. 4 shows a characteristic X-ray powder diffraction pattern (XRPD) of Pracinostat Form P4.

Crystalline Form P4 of Pracinostat may be characterized by each of the above characteristics alone or by all possible combinations, e.g., an XRPD pattern having peaks at 5.4, 10.8, 15.8, 21.8 and 25.6 degrees 2-theta±0.2 degrees 2-theta; an XRPD pattern as depicted in FIG. 4, and combinations thereof.

In one embodiment of the present disclosure, crystalline Form P4 of Pracinostat is isolated.

The present disclosure further includes a crystalline polymorph of Pracinostat, designated Form P6. The crystalline Form P6 of Pracinostat may be characterized by data selected from one or more of the following: an X-ray powder diffraction pattern substantially as depicted in FIG. 5; an X-ray powder diffraction pattern having peaks at 5.1, 5.8, 8.4, 10.1, and 16.1 degrees 2-theta±0.2 degrees 2-theta; a FTIR spectrum substantially as depicted in FIG. 19; and combinations of these data.

Crystalline Form P6 of Pracinostat may be further characterized by an X-ray powder diffraction pattern having peaks at 5.1, 5.8, 8.4, 10.1 and 16.1 degrees 2-theta±0.2 degrees 2-theta, and also having any one, two, three, four or five additional peaks selected from 15.4, 18.1, 20.4, 21.1 and 23.5 degrees 2-theta±0.2 degrees 2-theta.

Figure 5:
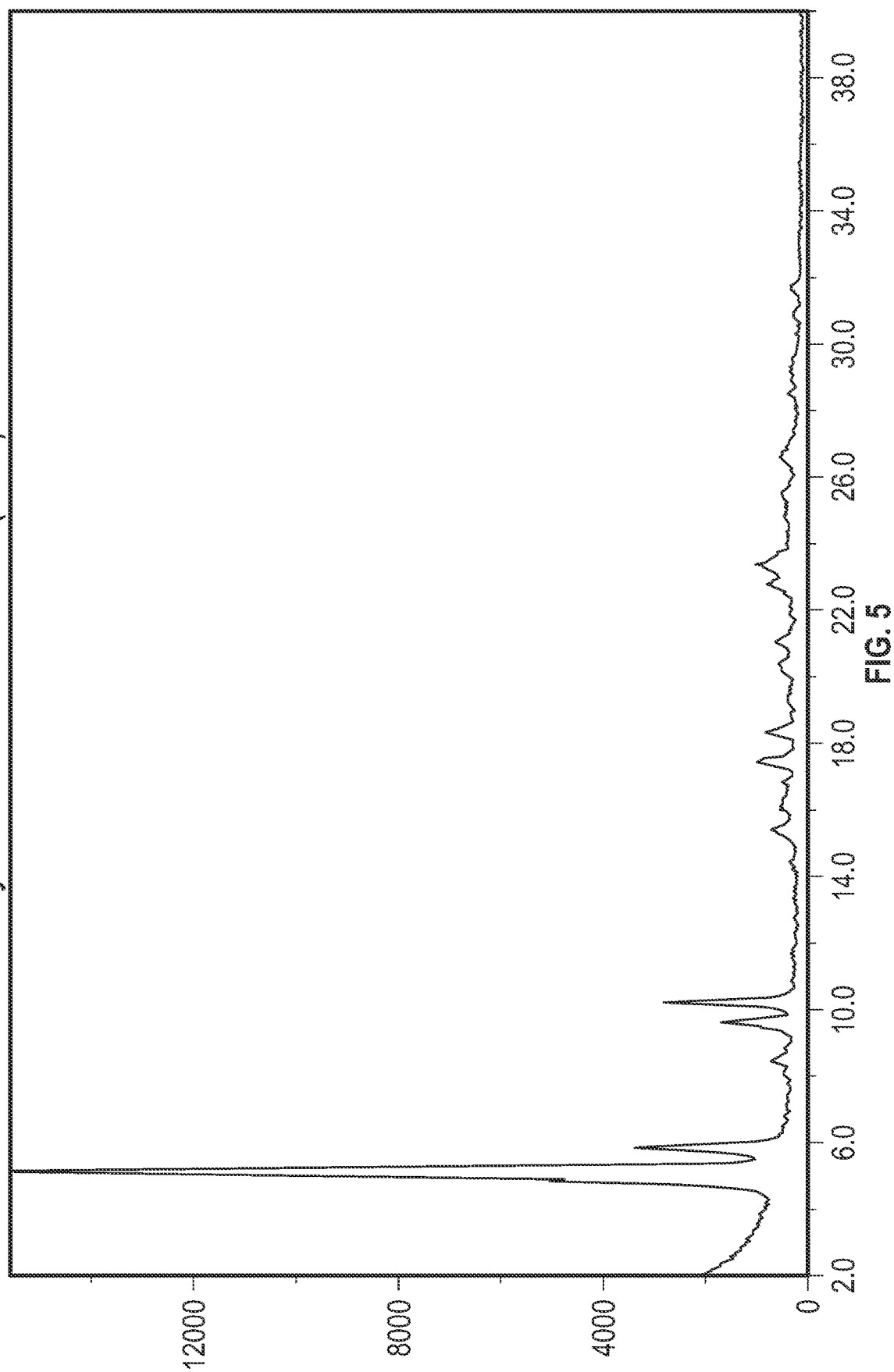
FIG. 5 shows characteristic X-ray powder diffraction pattern (XRPD) of Pracinostat Form P6.

Crystalline Form P6 of Pracinostat may be characterized by each of the above characteristics alone or by all possible combinations, e.g., an XRPD pattern having peaks at 5.1, 5.8, 8.4, 10.1 and 16.1 degrees 2-theta±0.2 degrees 2-theta; an XRPD pattern as depicted in FIG. 5, and combinations thereof.

In one embodiment of the present disclosure, crystalline Form P6 of Pracinostat is isolated.

The present disclosure further includes a crystalline polymorph of Pracinostat, designated Form P7. The crystalline Form P7 of Pracinostat may be characterized by data selected from one or more of the following: an X-ray powder diffraction pattern substantially as depicted in FIG. 6; an X-ray powder diffraction pattern having peaks at 7.0, 15.6, 18.2, 19.5 and 24.6 degrees 2-theta±0.2 degrees 2-theta; a FTIR spectrum substantially as depicted in FIG. 20; and combinations of these data.

Crystalline Form P7 of Pracinostat may be further characterized by an X-ray powder diffraction pattern having peaks at 7.0, 15.6, 18.2, 19.5 and 24.6 degrees 2-theta±0.2 degrees 2-theta, and also having any one, two, three, four or five additional peaks selected from 14.3, 16.4, 18.8, 21.0 and 22.9 degrees 2-theta±0.2 degrees 2-theta.

Crystalline Form P7 of Pracinostat may be an anhydrous form.

Figure 6:
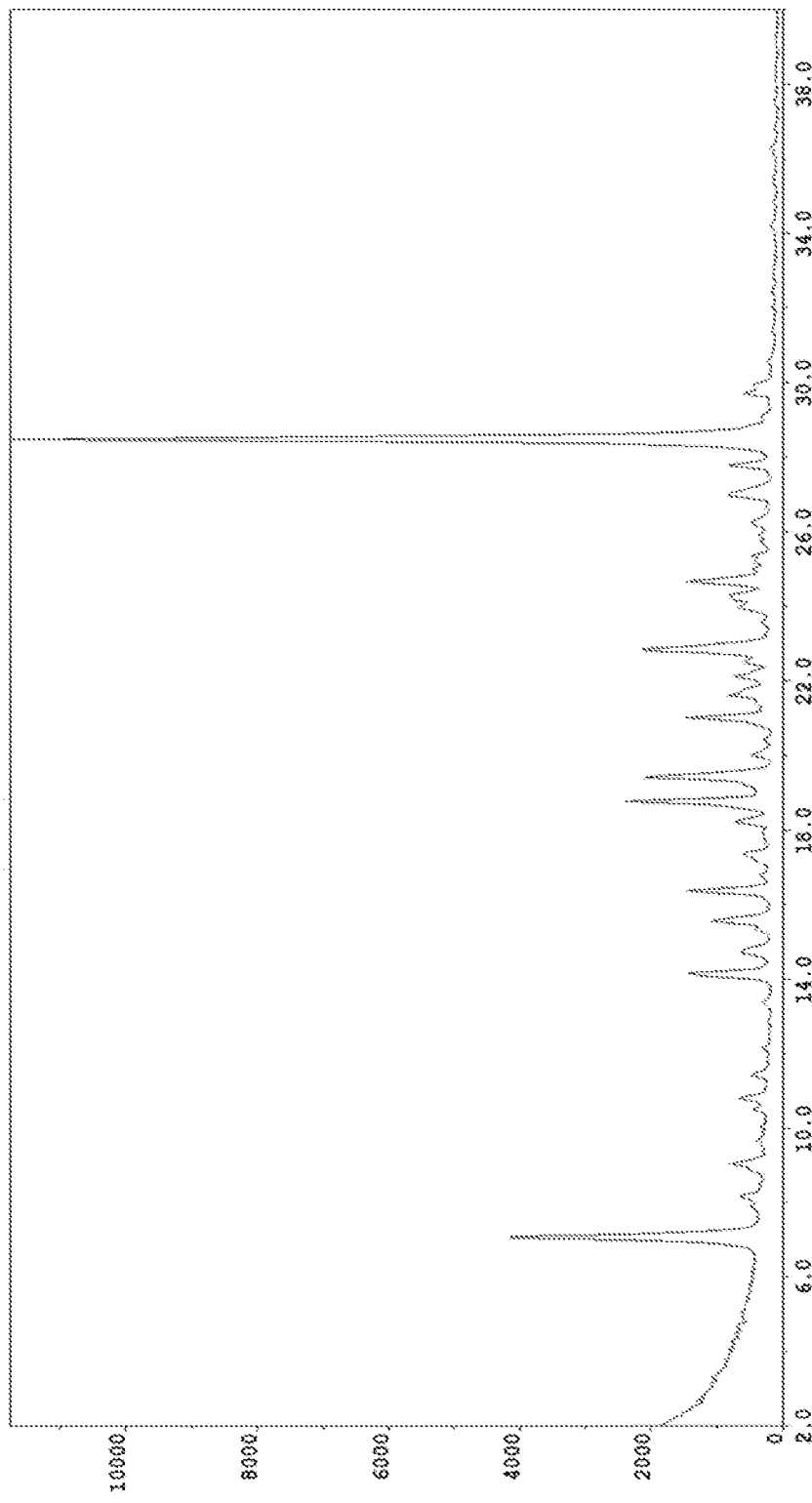
FIG. 6 shows characteristic X-ray powder diffraction pattern (XRPD) of Pracinostat Form P7.

Crystalline Form P7 of Pracinostat may be characterized by each of the above characteristics alone or by all possible combinations, e.g., an XRPD pattern having peaks at 7.0, 15.6, 18.2, 19.5 and 24.6 degrees 2-theta±0.2 degrees 2-theta; an XRPD pattern as depicted in FIG. 6, and combinations thereof.

In one embodiment of the present disclosure, crystalline Form P7 of Pracinostat is isolated.

The step of isolating Pracinostat or crystalline polymorph of Pracinostat may be performed by crystallization.

Crystalline Form P7 of Pracinostat may have any one of the above-described advantageous properties. For example, Form P7 is stable under grinding, physical pressure and thermal tests. In addition, it is non-hygroscopic, i.e. it absorb water to the extent of less than 0.2% (w/w) and it is polymorphically stable RH of from 0% to 100%, for a period of at least 7 days, at room temperature.

The present disclosure further includes a crystalline polymorph of Pracinostat, designated Form P8. The crystalline Form P8 of Pracinostat may be characterized by data selected from one or more of the following: an X-ray powder diffraction pattern substantially as depicted in FIG. 7; an X-ray powder diffraction pattern having peaks at 5.0, 10.2, 11.9, 18.5 and 19.7 degrees 2-theta±0.2 degrees 2-theta; and combinations of these data.

Crystalline Form P8 of Pracinostat may be further characterized by an X-ray powder diffraction pattern having peaks at 5.0, 10.2, 11.9, 18.5 and 19.7 degrees 2-theta±0.2 degrees 2-theta, and also having any one, two, three, four or five additional peaks selected from 10.7, 11.1, 12.3, 20.7 and 22.8 degrees 2-theta±0.2 degrees 2-theta.

Figure 7:
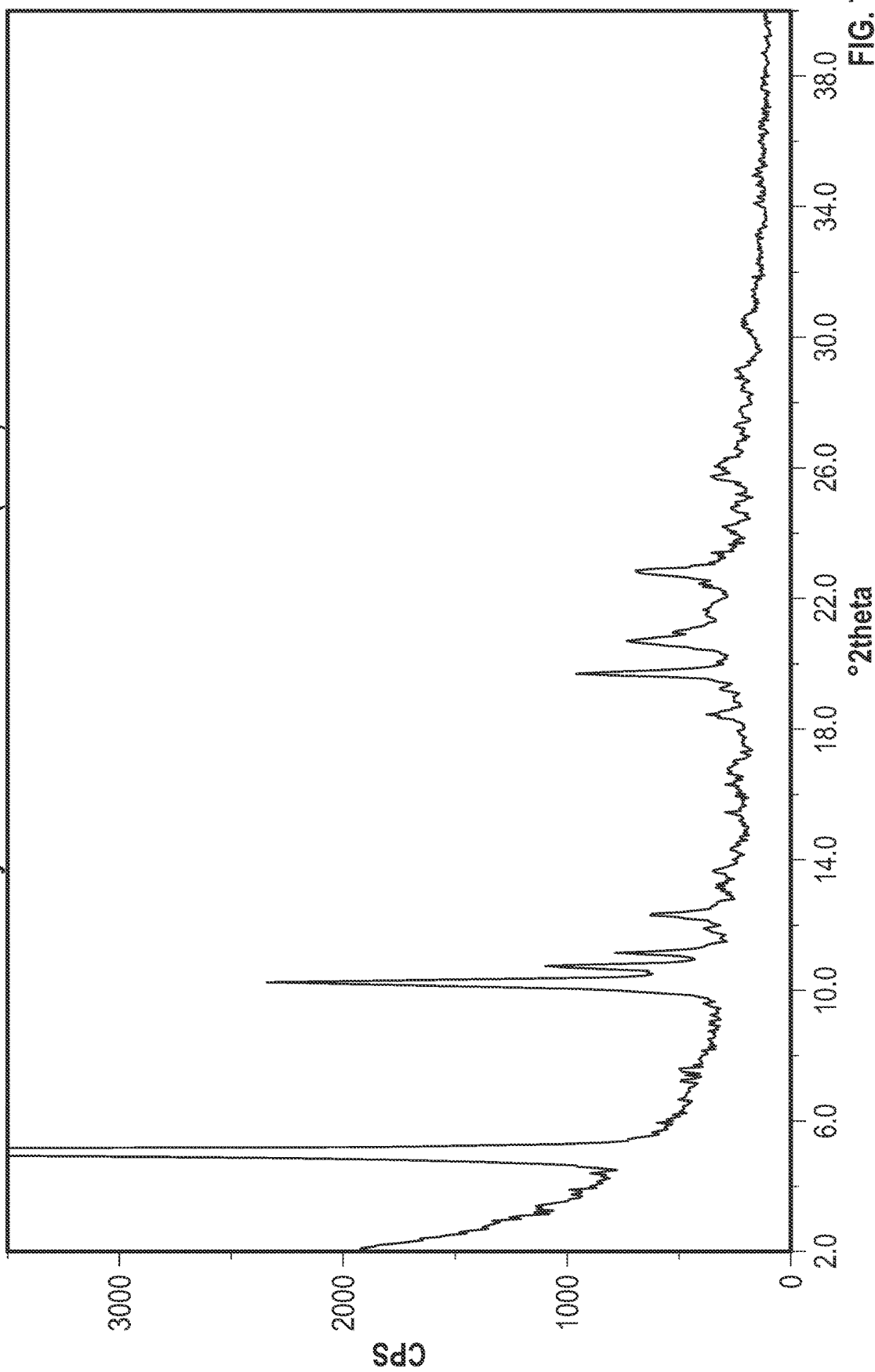
FIG. 7 shows characteristic X-ray powder diffraction pattern (XRPD) of Pracinostat Form P8.

Crystalline Form P8 of Pracinostat may be characterized by each of the above characteristics alone or by all possible combinations, e.g., an XRPD pattern having peaks at 5.0, 10.2, 11.9, 18.5 and 19.7 degrees 2-theta±0.2 degrees 2-theta; an XRPD pattern as depicted in FIG. 7, and combinations thereof In one embodiment of the present disclosure, crystalline Form P8 of Pracinostat is isolated.

The step of isolating Pracinostat or crystalline polymorph of Pracinostat may be performed by crystallization.

The present disclosure also provides crystalline Pracinostat polymorphs in solvate form.

The present disclosure further includes a crystalline polymorph of Pracinostat, which is a formic acid solvate of Pracinostat, designated Form F1. The crystalline Form F1 of Pracinostat formic acid solvate may be characterized by data selected from one or more of the following: an X-ray powder diffraction pattern substantially as depicted in FIG. 8; an X-ray powder diffraction pattern having peaks at 5.8, 9.3, 12.4, 21.2 and 22.4 degrees 2-theta±0.2 degrees 2-theta; and combinations of these data.

Crystalline Form F1 of Pracinostat formic acid solvate may be further characterized by an X-ray powder diffraction pattern having peaks at 5.8, 9.3, 12.4, 21.2 and 22.4 degrees 2-theta±0.2 degrees 2-theta, and also having any one, two, three, four or five additional peaks selected from 5.3, 11.7, 17.6, 23.8 and 25.3 degrees 2-theta±0.2 degrees 2-theta.

Figure 8:
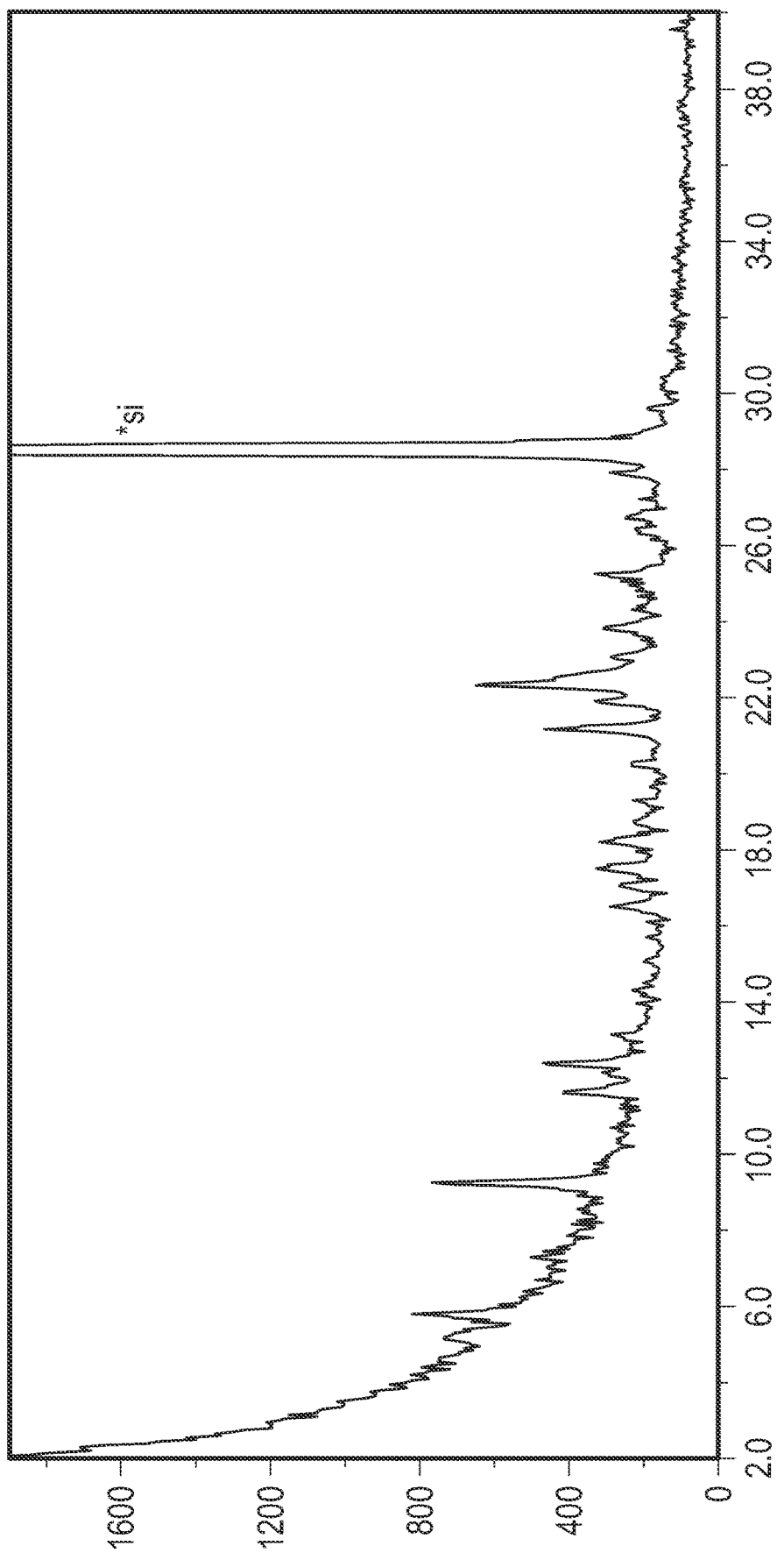
FIG. 8 shows characteristic X-ray powder diffraction pattern (XRPD) of Pracinostat formic acid solvate Form F1.

Crystalline Form F1 of Pracinostat formic acid solvate may be characterized by each of the above characteristics alone or by all possible combinations, e.g., an XRPD pattern having peaks at 5.8, 9.3, 12.4, 21.2 and 22.4 degrees 2-theta±0.2 degrees 2-theta; an XRPD pattern as depicted in FIG. 8, and combinations thereof.

In one embodiment of the present disclosure, Form F1 of Pracinostat formic acid solvate is isolated.

The step of isolating Pracinostat formic acid solvate may be performed by crystallization.

The present disclosure further includes a crystalline polymorph of Pracinostat, which is an acetic acid solvate of Pracinostat, designated Form A1. The crystalline Form A1 of Pracinostat acetic acid solvate may be characterized by data selected from one or more of the following: an X-ray powder diffraction pattern substantially as depicted in FIG. 9; an X-ray powder diffraction pattern having peaks at 5.8, 15.4, 16.5, 20.2 and 23.3 degrees 2-theta±0.2 degrees 2-theta; and combinations of these data.

Crystalline Form A1 of Pracinostat acetic acid solvate may be further characterized by an X-ray powder diffraction pattern having peaks at 5.8, 15.4, 16.5, 20.2 and 23.3 degrees 2-theta±0.2 degrees 2-theta, and also having any one, two, three, four or five additional peaks selected from 8.4, 10.2, 14.3, 24.8 and 25.4 degrees 2-theta±0.2 degrees 2-theta.

Figure 9:
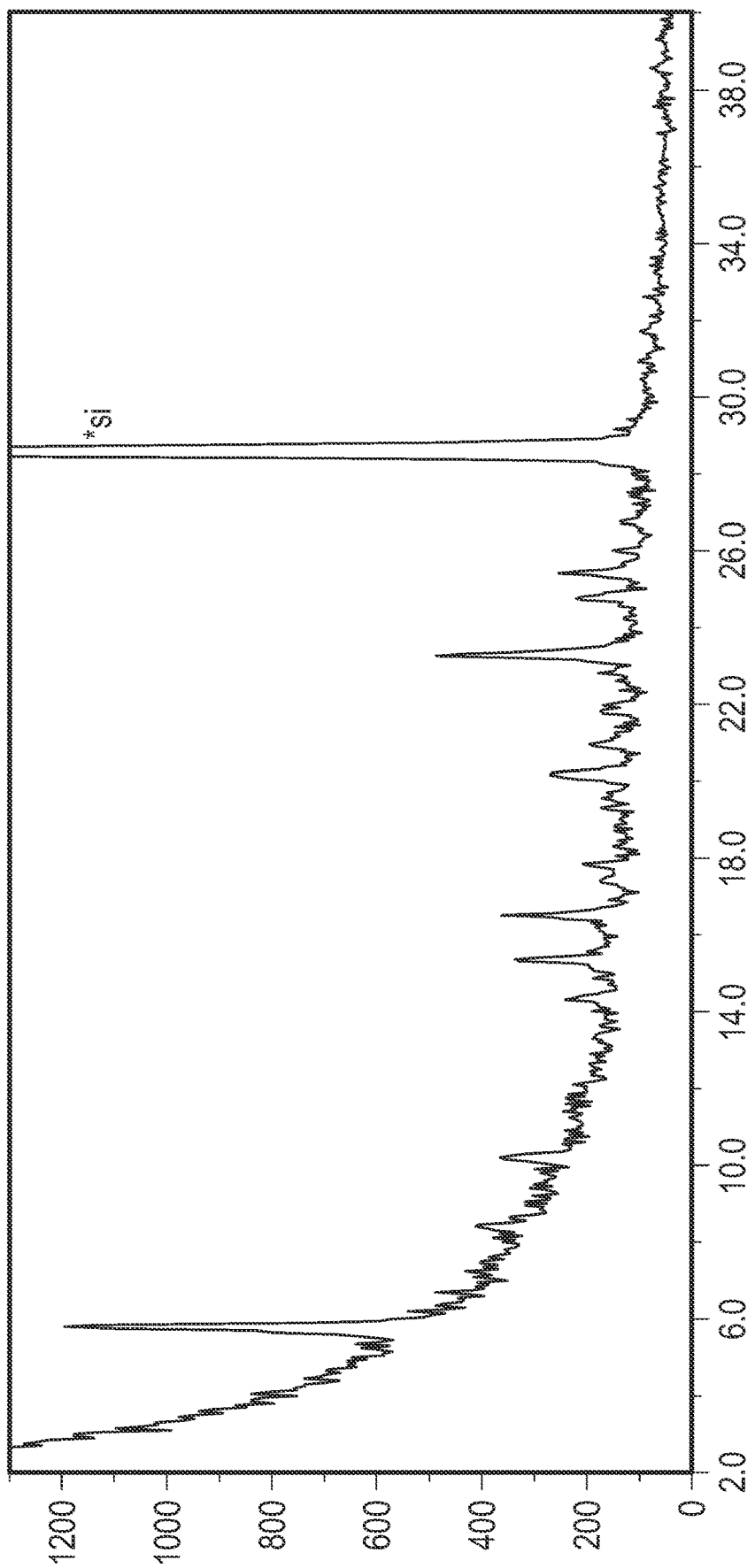
FIG. 9 shows characteristic X-ray powder diffraction pattern (XRPD) of Pracinostat acetic acid solvate Form A1.

Crystalline Form A1 of Pracinostat acetic acid solvate may be characterized by each of the above characteristics alone or by all possible combinations, e.g., an XRPD pattern having peaks at 5.8, 15.4, 16.5, 20.2 and 23.3 degrees 2-theta±0.2 degrees 2-theta; an XRPD pattern as depicted in FIG. 9, and combinations thereof In one embodiment of the present disclosure, Form A1 of Pracinostat acetic acid solvate is isolated.

The step of isolating Pracinostat acetic acid solvate may be performed by crystallization.

The present disclosure further includes a crystalline polymorph of Pracinostat, which is a butyric acid solvate of Pracinostat, designated Form B1. The crystalline Form B1 of Pracinostat butyric acid solvate may be characterized by data selected from one or more of the following: an X-ray powder diffraction pattern substantially as depicted in FIG. 11; an X-ray powder diffraction pattern having peaks at 6.7, 7.3, 8.3, 12.9 and 20.2 degrees 2-theta±0.2 degrees 2-theta; and combinations of these data.

Crystalline Form B1 of Pracinostat butyric acid solvate may be further characterized by an X-ray powder diffraction pattern having peaks at 6.7, 7.3, 8.3, 12.9 and 20.2 degrees 2-theta±0.2 degrees 2-theta, and also having any one, two, three, four or five additional peaks selected from 4.6, 5.3, 9.4, 12.0 and 14.6 degrees 2-theta±0.2 degrees 2-theta.

Figure 11:
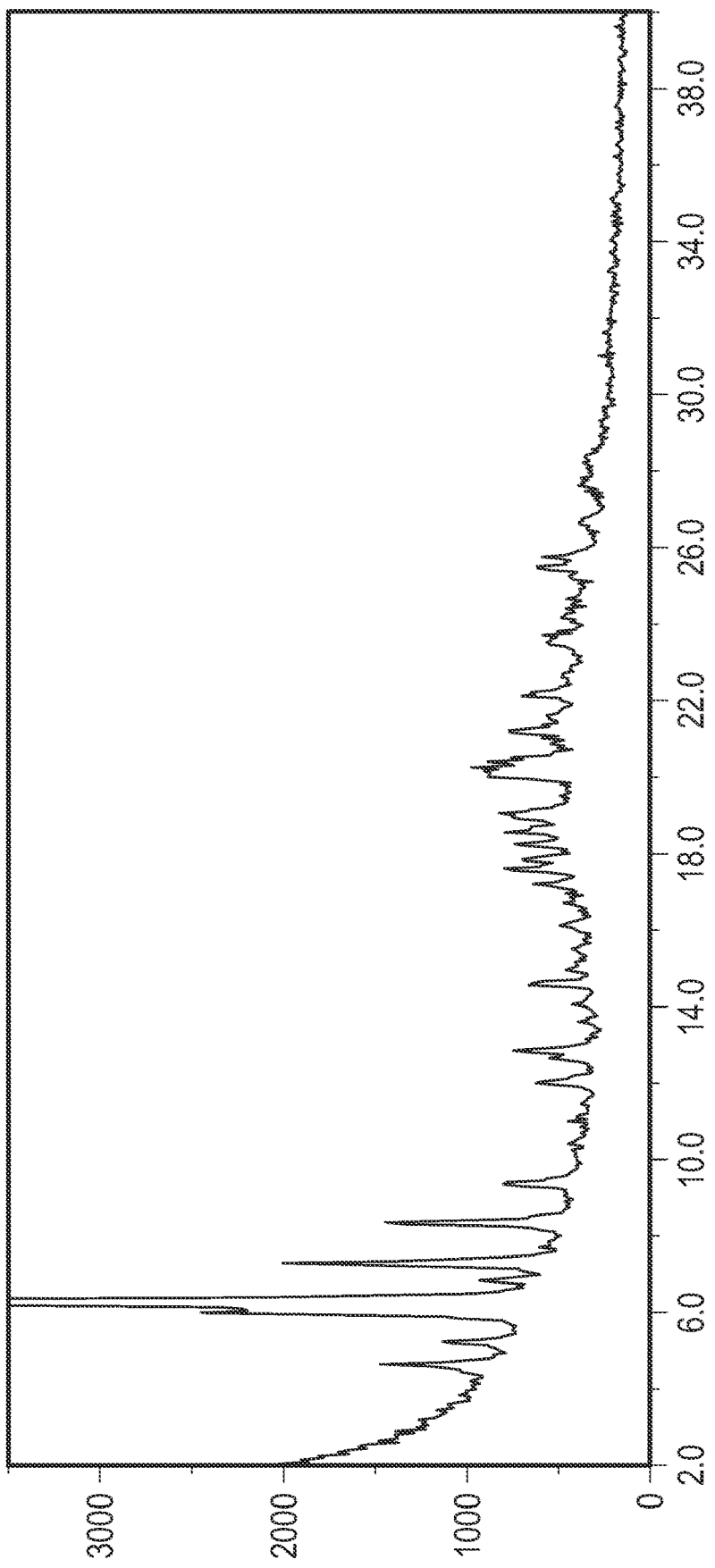
FIG. 11 shows characteristic X-ray powder diffraction pattern (XRPD) of Pracinostat butyric acid solvate Form B1.

Crystalline Form B1 of Pracinostat butyric acid solvate may be characterized by each of the above characteristics alone or by all possible combinations, e.g., an XRPD pattern having peaks at 6.7, 7.3, 8.3, 12.9 and 20.2 degrees 2-theta±0.2 degrees 2-theta; an XRPD pattern as depicted in FIG. 11, and combinations thereof.

In one embodiment of the present disclosure, Form B1 of Pracinostat butyric acid solvate is isolated.

The step of isolating Pracinostat butyric acid solvate may be performed by crystallization.

The present disclosure further includes a crystalline polymorph of Pracinostat, which is an iso-butyric acid solvate of Pracinostat, designated Form IB1. The crystalline Form IB1 of Pracinostat iso-butyric acid solvate may be characterized by data selected from one or more of the following: an X-ray powder diffraction pattern substantially as depicted in FIG. 12; an X-ray powder diffraction pattern having peaks at 4.8, 5.9, 6.9, 8.4 and 20.7 degrees 2-theta±0.2 degrees 2-theta; and combinations of these data.

Crystalline Form IB1 of Pracinostat iso-butyric acid solvate may be further characterized by an X-ray powder diffraction pattern having peaks at 4.8, 5.9, 6.9, 8.4 and 20.7 degrees 2-theta±0.2 degrees 2-theta, and also having any one, two, three, four or five additional peaks selected from 10.3, 11.9, 13.1, 15.6 and 16.9 degrees 2-theta±0.2 degrees 2-theta.

Figure 12:
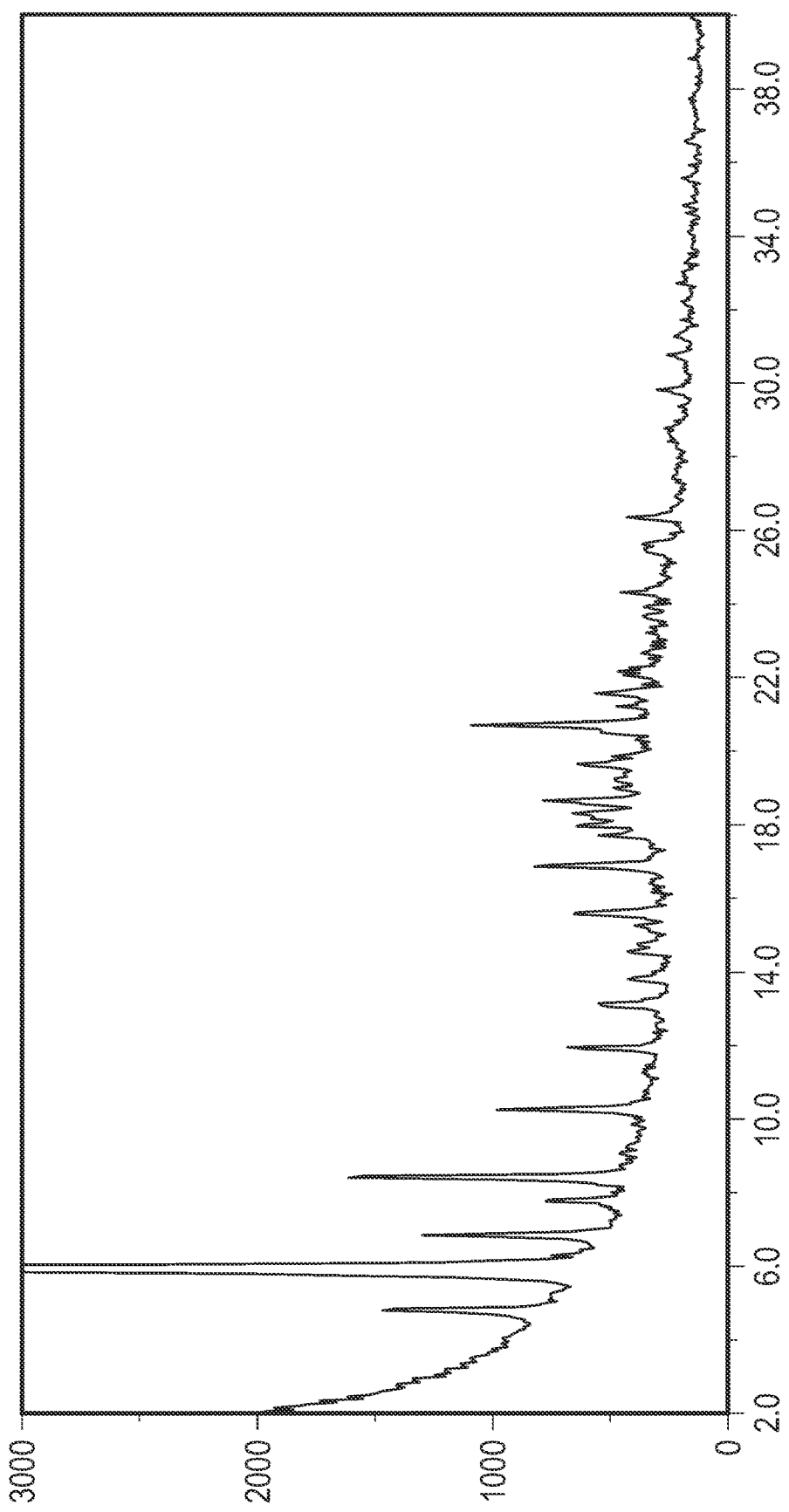
FIG. 12 shows characteristic X-ray powder diffraction pattern (XRPD) of Pracinostat iso-butyric acid solvate Form IB1.

Crystalline Form IB1 of Pracinostat iso-butyric acid solvate may be characterized by each of the above characteristics alone or by all possible combinations, e.g., an XRPD pattern having peaks at 4.8, 5.9, 6.9, 8.4 and 20.7 degrees 2-theta±0.2 degrees 2-theta; an XRPD pattern as depicted in FIG. 12, and combinations thereof In one embodiment of the present disclosure, Form IB1 of Pracinostat iso-butyric acid solvate is isolated.

The step of isolating Pracinostat iso-butyric acid solvate Form IB1 may be performed by crystallization.

The present disclosure further includes a crystalline polymorph of Pracinostat, designated Form I1. The crystalline Form I1 of Pracinostat may be characterized by data selected from one or more of the following: an X-ray powder diffraction pattern substantially as depicted in FIG. 23; an X-ray powder diffraction pattern having peaks at 5.3, 6.2, 14.6, 18.3 and 26.7 degrees 2-theta±0.2 degrees 2-theta; and combinations of these data.

Crystalline Form I1 of Pracinostat may be further characterized by an X-ray powder diffraction pattern having peaks at 5.3, 6.2, 14.6, 18.3 and 26.7 degrees 2-theta±0.2 degrees 2-theta, and also having any one, two, three, four or five additional peaks selected from 8.2, 9.6, 16.2, 18.7 and 23.5 degrees 2-theta±0.2 degrees 2-theta.

Crystalline Form I1 of Pracinostat may be a butyric acid or iso-butyric acid solvate.

Figure 23:
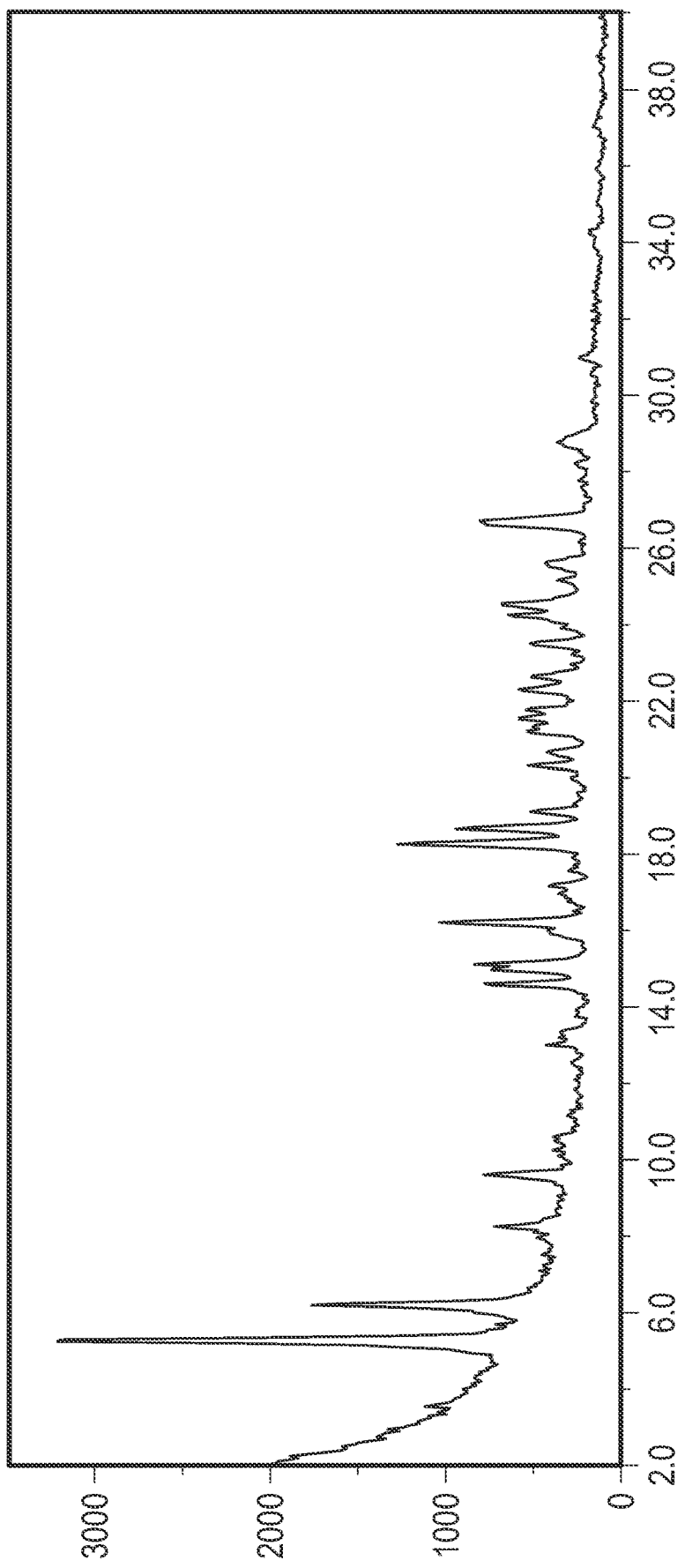
FIG. 23 shows characteristic X-ray powder diffraction pattern (XRPD) of Pracinostat Form I1 (as butyric acid solvate).

Crystalline Form I1 of Pracinostat may be characterized by each of the above characteristics alone or by all possible combinations, e.g., an XRPD pattern having peaks at 5.3, 6.2, 14.6, 18.3 and 26.7 degrees 2-theta±0.2 degrees 2-theta; an XRPD pattern as depicted in FIG. 23, and combinations thereof.

In one embodiment of the present disclosure, Form I1 of Pracinostat is isolated.

The step of isolating Form I1 of Pracinostat may be performed by crystallization.

The present disclosure further includes a crystalline polymorph of Pracinostat, designated Form I2. The crystalline Form I2 of Pracinostat may be characterized by data selected from one or more of the following: an X-ray powder diffraction pattern substantially as depicted in FIG. 24; an X-ray powder diffraction pattern having peaks at 4.8, 5.3, 6.8, 10.2 and 15.1 degrees 2-theta±0.2 degrees 2-theta; and combinations of these data.

Crystalline Form I2 of Pracinostat may be further characterized by an X-ray powder diffraction pattern having peaks at 4.8, 5.3, 6.8, 10.2 and 15.1 degrees 2-theta±0.2 degrees 2-theta, and also having any one, two, three, four or five additional peaks selected from 5.9, 12.1, 16.1, 18.3 and 20.6 degrees 2-theta±0.2 degrees 2-theta.

Crystalline Form I2 of Pracinostat may be a butyric acid or iso-butyric acid solvate.

Crystalline Form I2 of Pracinostat may be characterized by each of the above characteristics alone or by all possible combinations, e.g., an XRPD pattern having peaks at 4.8, 5.3, 6.8, 10.2 and 15.1 degrees 2-theta±0.2 degrees 2-theta; an XRPD pattern as depicted in FIG. 24, and combinations thereof.

In one embodiment of the present disclosure, Form I2 of Pracinostat is isolated.

The step of isolating Form I2 of Pracinostat may be performed by crystallization.

In addition, the present disclosure comprises Pracinostat sulfate salt, particularly in crystalline form.

Figure 15A:
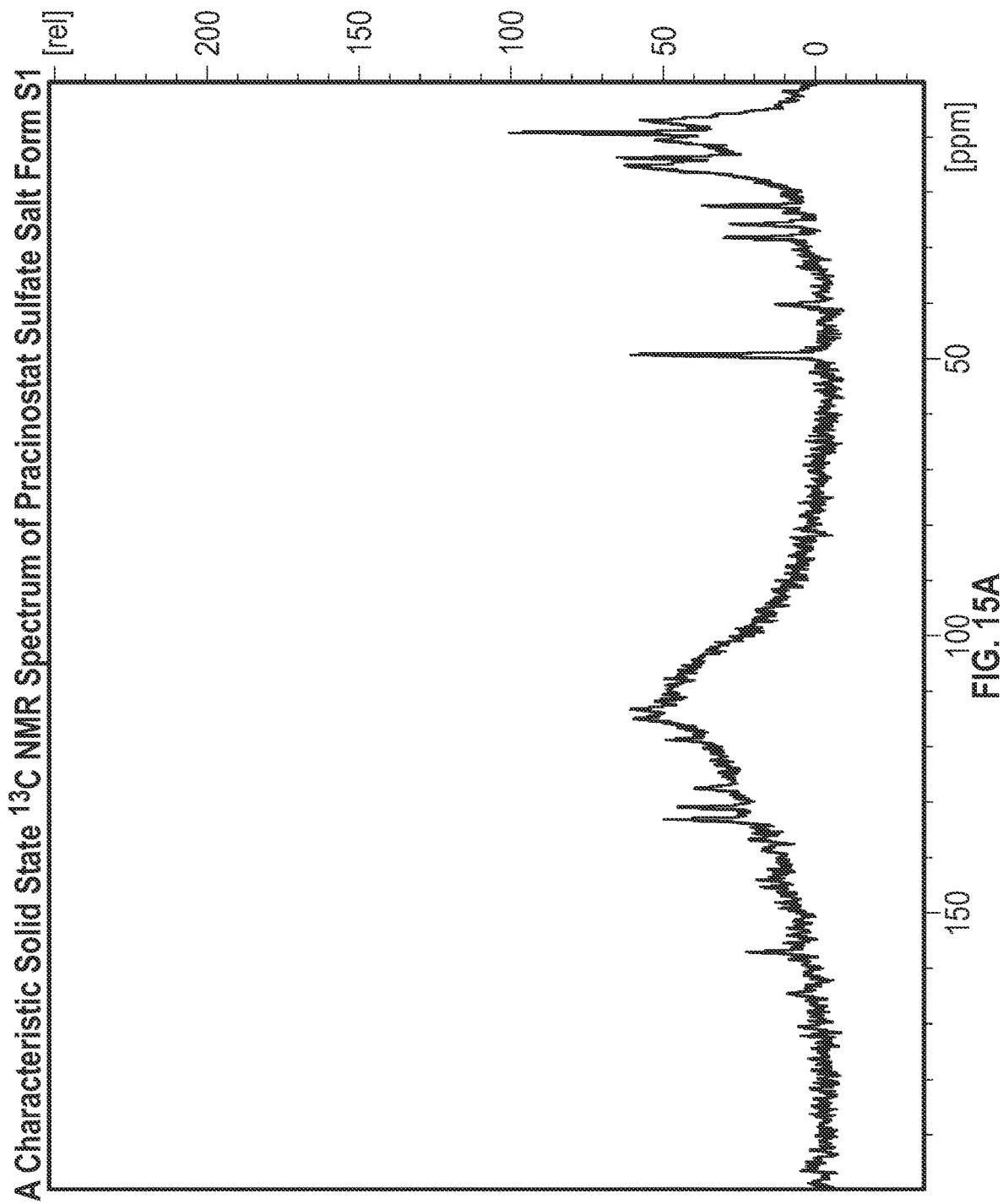
FIG. 15a shows characteristic solid state $^{13}$C NMR of Pracinostat sulfate salt Form S1.
Figure 15B:
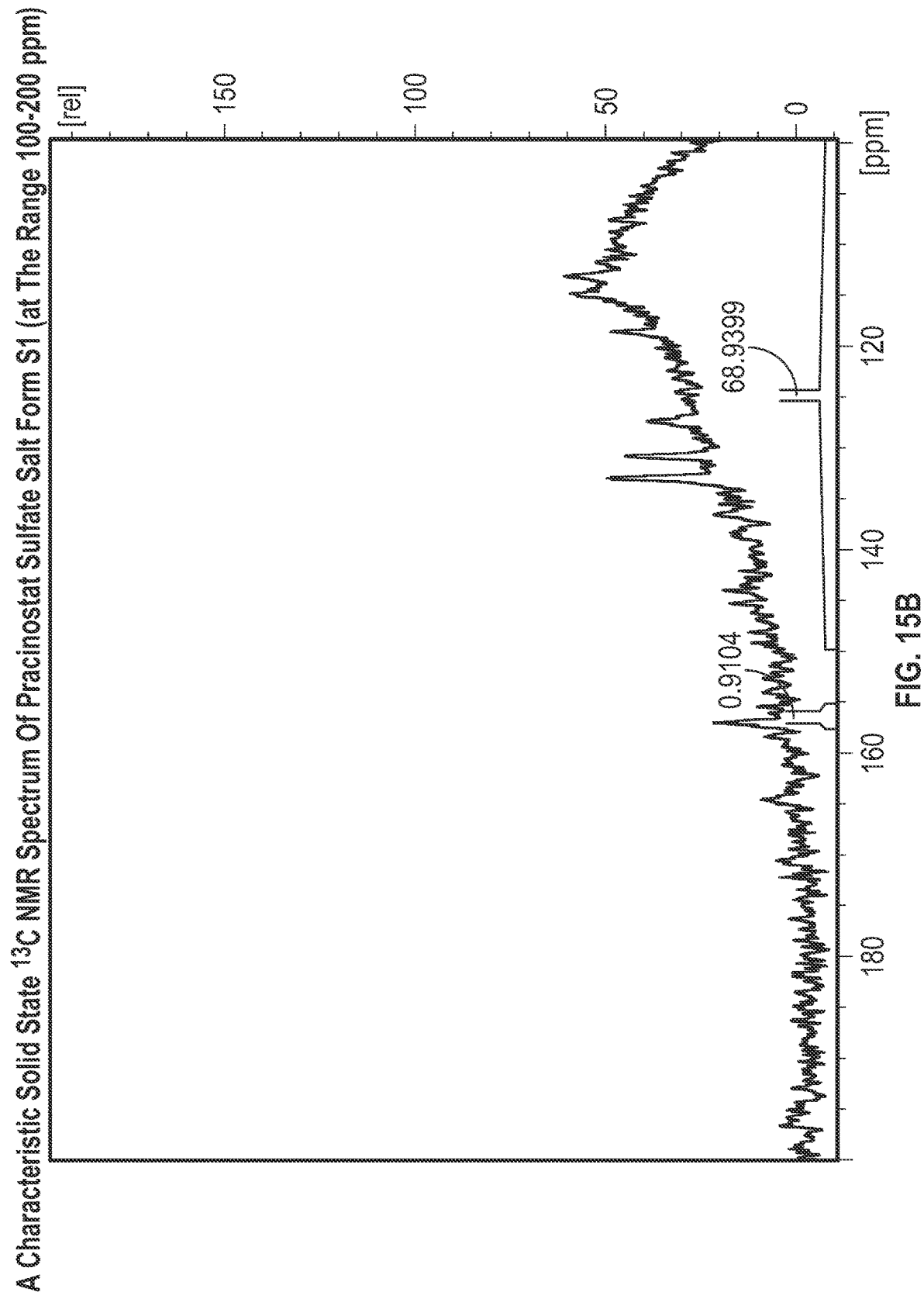
FIG. 15b shows characteristic solid state $^{13}$C NMR of Pracinostat sulfate salt Form S1 (at the range 100-200 ppm).

The present disclosure further includes a crystalline polymorph of Pracinostat sulfate salt, designated Form S1. The crystalline Form S1 of Pracinostat sulfate may be characterized by data selected from one or more of the following: an X-ray powder diffraction pattern substantially as depicted in FIG. 10; an X-ray powder diffraction pattern having peaks at 17.5, 21.0, 23.2, 23.7 and 26.8 degrees 2-theta±0.2 degrees 2-theta; a solid state $^{13}$C NMR spectrum substantially as depicted in any one of FIGS. 15a, 15b and 15c; a solid state $^{13}$C NMR spectrum having peaks at the range of 100-200 ppm at 133.04 m 130.73, 127.41, 118.54 and 113.14 ppm±2 ppm; a solid state $^{13}$C NMR spectrum having the following chemical shift absolute differences from a peak at 156.95 ppm±2 ppm of 23.91, 26.22, 29.54, 38.41 and 43.81 ppm±2 ppm; a solid state $^{13}$C NMR spectrum having chemical shift difference from a peak at 156.95 ppm±1 ppm to 133.04 ppm±1 ppm of 23.9 ppm±1 ppm; a FTR spectrum substantially as depicted in FIG. 21; and combinations of these data.

Crystalline Form S1 of Pracinostat sulfate may be further characterized by an X-ray powder diffraction pattern having peaks at 17.5, 21.0, 23.2, 23.7 and 26.8 degrees 2-theta±0.2 degrees 2-theta, and also having any one, two, three, four or five additional peaks selected from 11.6, 12.3, 15.4, 24.8 and 25.7 degrees 2-theta±0.2 degrees 2-theta.

Crystalline Form S1 of Pracinostat sulfate may possess water content of from about 2.6 to about 5.0, in embodiments about 2.7% as measured by KF. Accordingly, Form S1 may be a hydrate, particularly a monohydrate.

Figure 10:
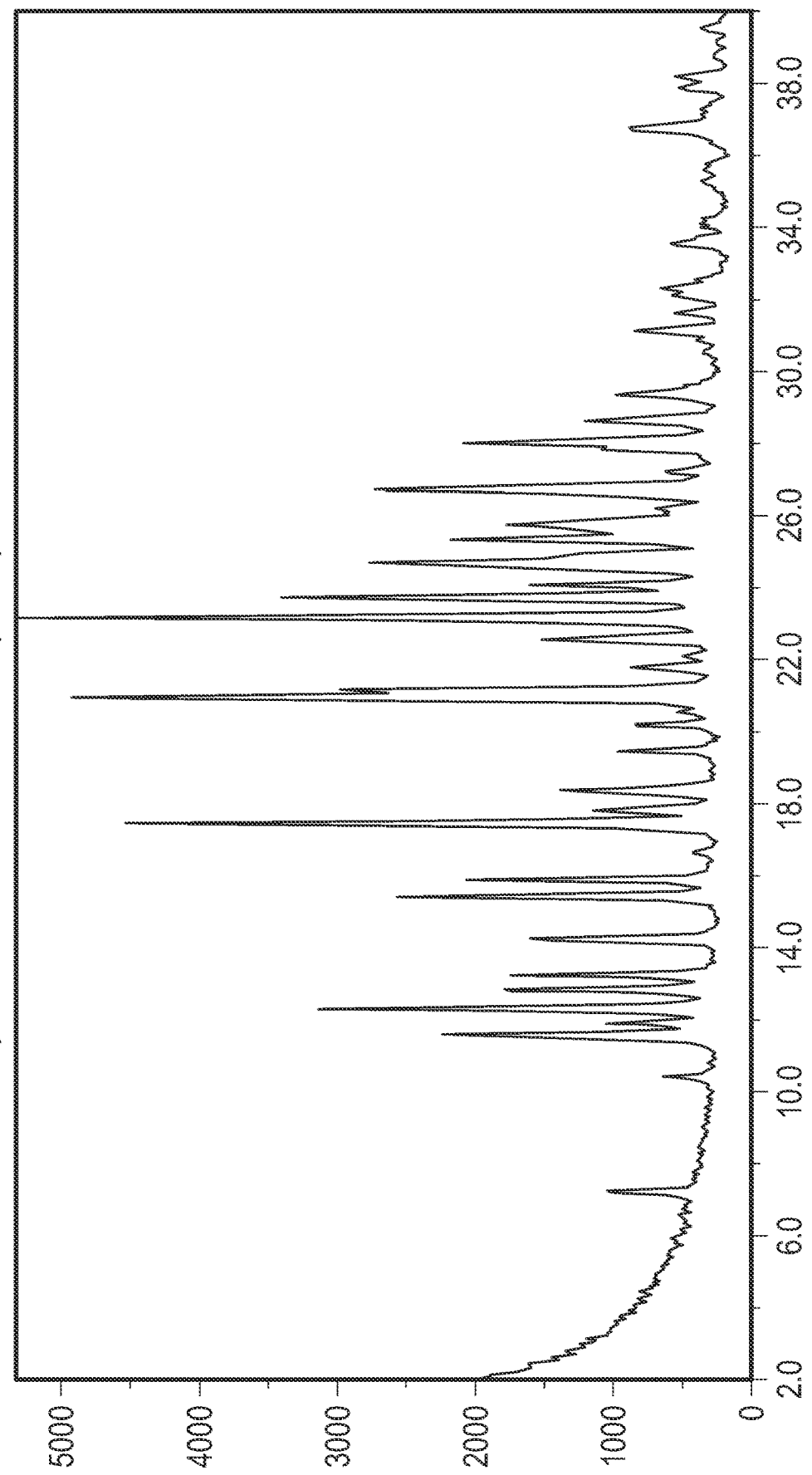
FIG. 10 shows characteristic X-ray powder diffraction pattern (XRPD) of Pracinostat sulfate salt Form salt S1.

Crystalline Form S1 of Pracinostat sulfate may be characterized by each of the above characteristics alone or by all possible combinations, e.g., an XRPD pattern having peaks at 17.5, 21.0, 23.2, 23.7 and 26.8 degrees 2-theta±0.2 degrees 2-theta; an XRPD pattern as depicted in FIG. 10, and combinations thereof.

In one embodiment of the present disclosure, Form S1 of Pracinostat sulfate is isolated.

The step of isolating Pracinostat sulfate or crystalline polymorph of Pracinostat may be performed by crystallization.

Crystalline Form S1 of Pracinostat sulfate may have any one of the above described advantageous properties. For example, Pracinostat sulfate Form S1 is stable under grinding, physical pressure and thermal tests. In addition, it is slightly hygroscopic, i.e. it absorb water to the extent of less than 2% (w/w) and it is polymorphically stable at RH of from 0% to 100%, for a period of at least 7 days, at room temperature.

The above crystalline polymorphs and solvates of Pracinostat and of Pracinostat salts can be used to prepare other crystalline polymorphs of Pracinostat, other Pracinostat salts and their solid state forms thereof.

The present disclosure provides crystalline polymorphs of Pracinostat and of Pracinostat salts for use in the preparation of pharmaceutical compositions including Pracinostat or Pracinostat salts and/or crystalline polymorphs thereof.

The present disclosure also encompasses the use of crystalline polymorphs of Pracinostat and of Pracinostat salts of the present disclosure for the preparation of pharmaceutical compositions of crystalline polymorphs Pracinostat or Pracinostat salts and/or crystalline polymorphs thereof.

The present disclosure includes processes for preparing the above-mentioned pharmaceutical compositions. The processes include combining any one or a combination of the crystalline polymorphs of Pracinostat and/or Pracinostat salts of the present disclosure with at least one pharmaceutically acceptable excipient.

Pharmaceutical formulations of the present invention contain any one or a combination of the solid state forms of Pracinostat or Pracinostat salts of the present disclosure. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, Pracinostat or Pracinostat salt and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity-enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration of the present disclosure is oral. The dosages can be conveniently presented in unit dosage form and prepared by any methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, in embodiments a powdered or granulated solid composition of the present disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, in embodiments water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can include any of the aforementioned blends and granulates that were described with reference to tableting, but they are not subjected to a final tableting step.

A pharmaceutical formulation of Pracinostat or Pracinostat salt can be administered. Pracinostat or Pracinostat salt may be formulated for administration to a mammal, preferably a human, by injection. Pracinostat or Pracinostat salt can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Pracinostat and of Pracinostat salts, and the pharmaceutical compositions of Pracinostat and of Pracinostat salts of the present disclosure, can be used as medicaments, in embodiments in the treatment of acute myeloid leukemia.

The present disclosure also provides methods of treating acute myeloid leukemia by administering a therapeutically effective amount of any one or a combination of the crystalline polymorphs of Pracinostat and/or Pracinostat salts of the present disclosure, or at least one of the above pharmaceutical compositions and/or formulations, to a subject in need of the treatment.

Having thus described the disclosure with reference to particular exemplary embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

XRPD Method

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min or 2 deg/min.

Solid State $^{13}$C-NMR Method

Solid-state 13C NMR spectra were recorded with variable amplitude cross polarization, magic angle spinning and high power proton decoupling using a BRUKER Avance II+ spectrometer operating at 125 MHz and controlled temperature at 0° C. A probe using 4 mm o.d. zirconia rotors was employed. The operation conditions were: contact time: 2 ms; recycle delay: 5 s; 1024 scans and spin rate of 11 kHz. Chemical shifts were referenced via a replacement sample of glycine (carboxyl carbon chemical shift assigned as 176.03 ppm relative to the signal of tetramethylsilane).

FTIR Method

Equipment: Nicolet iS5 by Themofisher scientific. Analysis parameters: The samples were studied in ATR model (iD7). The spectrum was scanned between 4000-400 cm-1. All the spectra were measured in 16 scans.

Grinding, Physical Pressure and Thermal Tests

Grinding stability test: The tested sample was grinded by moltal&pestle for 1 minute at room temperature either without a solvent or with one drop of solvent from the following solvents: Ethanol, Isopropyl alcohol and water.

Physical pressure stability test: The tested sample was exposed to 3 ton pressure for 1 minute at room temperature.

Thermal stability test: The tested sample was heated to temperature of 100° C. for 30 minutes at open dish.

Preparation of Starting Materials

Pracinostat can be prepared according to methods known from the literature (for example WO 2007/30080).

Example 1. Preparation of Pracinostat Form P1

About 50 mg of Pracinostat form P2 were slurried with water (500 μL, 10 vol) using magnetic stirrer in a sealed Vial at 90° C. overnight. The slurry was filtered to give a solid. The obtained solid was characterized by X-ray powder diffractogram to give Pracinostat form P1. See FIG. 1.

Example 2. Preparation of Pracinostat Form P2

MeOH (500 μL, 10 vol) was added to about 50 mg of Pracinostat. Both were mixed in a vial using magnetic stirrer and heated to 60° C. to give a clear solution. The solution was concentrated and dried under reduced pressure at 30° C. in a vacuum oven dryer for overnight to give a solid. The obtained solid was characterized by X-ray powder diffractogram to give Pracinostat form P2. See FIG. 2.

Example 3. Preparation of Pracinostat Form P3

About 50 mg of Pracinostat form P2 were slurried with 2-ethoxyethanol (500 μL, 10 vol) in a sealed vial at RT overnight using magnetic stirrer. The slurry was filtered to give a solid. The obtained solid was characterized by X-ray powder diffractogram to give Pracinostat form P3. See FIG. 3.

Example 4. Preparation of Pracinostat Form P3

A 500 μl of EtOH was added to 1 ml vial that contains about 50 mg of Pracinostat form P2. The slurry was stirred by magnetic stirrer at 90° C. for a few minutes to obtain clear solution. The clear solution was cooled to RT and stirred at RT for 18 hours. After that, the obtained solid was filtered by centrifugation. This obtained solid was characterized by X-ray powder diffractogram to give Pracinostat form P3.

Example 5. Preparation of Pracinostat Form P3

A 500 μl of methyl ethyl ketone (MEK) was added to 1 ml vial that contains about 50 mg of Pracinostat form P2. The slurry was stirred by magnetic stirrer at 60° C. for 18 hours. After that, the obtained solid was filtered by centrifugation. This obtained solid was characterized by X-ray powder diffractogram to give Pracinostat form P3.

Example 6. Preparation of Pracinostat Form P4

About 50 mg of Pracinostat form P2 were slurried with ethanol (500 μL, 10 vol) using magnetic stirrer in a sealed vial at RT overnight. The slurry was filtered to give a solid. The obtained solid was characterized by X-ray powder diffractogram to give Pracinostat form P4. See FIG. 4.

Example 7. Preparation of Pracinostat Form P6

About 500 μl of methyl tert-butyl ether (MTBE) was added to 1 ml vial that contain about 50 mg of Pracinostat form P2. The slurry was stirred by magnetic stirrer at 60° C. for 18 h. After that, the obtained solid was filtered by centrifugation. This obtained solid was characterized by X-ray powder diffractogram to give Pracinostat form P6 (FIG. 5).

Example 8. Preparation of Pracinostat Form P7

About 500 mg of Pracinostat form P1 were dissolved with dimethyl sulfoxide (DMSO) (2.5 mL, 5 vol) in a 20 ml vial with magnetic stirrer at 60° C. After 15 min clear solution was obtained. A 140 μl of the obtained clear solution were transferred to 7 ml vial and 560 μl of Isobutyl acetate was added to the vial. The obtained clear solution of DMSO, Isobutyl acetate and Pracinostat was stirred at 4° C. for 72 hours. After that, the obtained solid was filtered by centrifugation. This obtained solid was characterized by X-ray powder diffractogram to give Pracinostat form P7 (FIG. 6).

Example 9. Preparation of Pracinostat Form P7

About 500 mg of Pracinostat form P1 were dissolved with DMSO (2.5 mL, 5 vol) in a 20 ml vial with magnetic stirrer at 60° C., after 15 min clear solution was obtained. About 140 μl of the obtained clear solution were transferred to 7 ml vial and about 280 μl of Heptane was added to the vial. The obtained clear solution of DMSO, Heptane and Pracinostat was stirred at 4° C. for 72 hours. After that, the obtained solid was filtered by centrifugation. This obtained solid was characterized by X-ray powder diffractogram to give Pracinostat form P7.

Example 10. Preparation of Pracinostat Form P7

About 500 mg of Pracinostat form P1 were dissolved with DMSO (2.5 mL, 5 vol) in a 20 ml vial with magnetic stirrer at 60° C., after 15 min clear solution was obtained. About 140 μl of the obtained clear solution were transferred to 7 ml vial and about 1.4 ml of Cyclohexane was added to the vial. The obtained clear solution of DMSO, Cyclohexane and Pracinostat was stirred at 4° C. for 72 hours. After that, the obtained solid was filtered by centrifugation. This obtained solid was characterized by X-ray powder diffractogram to give Pracinostat form P7.

Example 11. Preparation of Pracinostat Form P8

About 3.5 ml of solvent mixture (MeOH:DCM, 1:1) was added to 100 ml flask that contain 500 mg Pracinostat (Form P1). This mixture was stirred about 20 min at RT to obtain clear solution. After that about 3.5 ml double-distilled water (Analytical grade) was added to this clear solution to obtain oil fraction of Pracinostat. The solvents mixture (MeOH:DCM:H2O) was fast evaporated. The obtained solid was characterized by X-ray powder diffractogram to give Pracinostat form P8 (FIG. 7).

Example 12. Preparation of Pracinostat Formic Acid Solvate Form F1

A vial of 1 ml with magnetic stirrer was charge with Pracinostat form P1, Ethyl acetate (300 μL, 10 Vol) and formic acid (6.5 μL, 2.5 eq). This mixture was stirred at room temperature for 18 h. The obtained solid was filtered and dried over night under vacuum, at room temperature. This obtained crystal solid was characterized by X-ray powder diffractogram to give Pracinostat formic acid solvate Form F1 (FIG. 8).

Pracinostat formic acid solvate prepared in a similar manner was measured by TGA: Loss on drying (LOD): 26.76% at a temperature range of from about 79.9° C. to about 249.6° C.

Example 13. Preparation of Pracinostat Acetic Acid Solvate Form A1

A vial of 1 ml with magnetic stirrer was charge with Pracinostat form P1, Ethyl acetate (300 μL, 10 Vol) and acetic acid (8.4 μL, 2.5 eq). This mixture was stirred at room temperature for 18 h. The obtained solid was filtered and dried over night under vacuum, at room temperature. The obtained crystal solid was characterized by X-ray powder diffractogram to give Pracinostat acetic acid solvate Form A1 (FIG. 9).

Pracinostat acetic acid solvate prepared in a similar manner was measured by TGA: Loss on drying (LOD): 0.66% at a temperature range of from about 66.0° C. to about 120.6° C. and 13.27%. at a temperature range of from about 120.6° C. to about 248.9° C.

Example 14. Preparation of Pracinostat Sulfate Salt Form S1

A vial of 1 ml with magnetic stirrer was charge with Pracinostat form P1, methyl tetrahydrofuran (300 μL, 10 Vol) and sulfuric acid (13.8 μL, 2.5 eq). This mixture was stirred at room temperature for 18 h. The obtained solid was filtered and dried over night under vacuum, at room temperature. The obtained crystal solid was characterized by XRD to give Pracinostat sulfate salt Form S1 (FIG. 10).

Example 15. Preparation of Pracinostat Butyric Acid Solvate Form B1

Pracinostat P7 (25 mg) was placed in a glass tube and inserted to a vial filled with 2 ml of butyric acid. The vial was tightly closed for 1 week and after 1 week the sample was characterized by X-ray powder diffractogram to give Pracinostat butyric acid solvate form B1 as depicted in FIG. 11.

Example 16. Preparation of Pracinostat Iso-Butyric Acid Solvate Form IB1

Pracinostat P7 (25 mg) was placed in a glass tube and inserted to a vial filled with 2 ml of iso-butyric acid. The vial was tightly closed for 1 week and after 1 week the sample was characterized by X-ray powder diffractogram to give Pracinostat iso-butyric acid solvate form IB1 as depicted in FIG. 12.

Pracinostat iso-butyric acid solvate prepared in a similar manner was measured by TGA: Loss on drying (LOD): 1.05% at a temperature range of from about 31.2° C. to about 93.26° C. and 46.65% at a temperature range of from about 93.3° C. to about 248.4° C.

Example 17. Preparation of Pracinostat Form P1

Amyl alcohol (500 μL, 10 vol) was added to pracinostat (50 mg, 1.39 mmol, form P2) in a sealed vial to give slurry at room temperature. The obtained slurry was magnetically stirred and heated to 90° C. The slurry was stirred at 90° C. over a period of 18 hours. Then, the slurry was filtered by centrifugation and characterized by X-ray powder diffractogram as Pracinostat form P1.

Example 18. Preparation of Pracinostat Form P1

Pracinostat form P1 can be obtained in most slurry experiments that involves ethanol:water or isopropanol: water mixtures.

For example, a mixture of ethanol:water (500 µL, 10 vol, 7:3) was added to Pracinostat form P2 (50 mg, 0.139 mmol) in sealed vial to give slurry. The slurry was magnetically stirred at room temperature for 18 hours. Next, the slurry was filtered by centrifugation and characterized by X-ray powder diffractogram as Pracinostat form P.

Example 19. Preparation of Pracinostat Form P1

Ethylene glycol* (500 µL, 10 vol) was added to Pracinostat form P2 (50 mg, 0.139 mmol) in sealed vail to give slurry. The slurry was magnetically stirred at room temperature for 18 hours. Then, the slurry was filtered by centrifugation and characterized by X-ray powder diffractogram as Pracinostat form P1.
*This process can be done utilizing other solvents: amyl alcohol, isoamyl alcohol, ethylene glycol, propylene glycol and water.

Example 20. Preparation of Pracinostat Form P1

Water (500 µL, 10 vol) was added to Pracinostat form P7 (50 mg, 0.139 mmol) in sealed vail to give slurry. The slurry was magnetically stirred and heated to 90° C. The slurry was stirred at 90° C. during 18 hours. Then, the slurry was filtered by centrifugation and characterized by X-ray powder diffractogram as Pracinostat form P1.

Example 21. Preparation of Pracinostat Form P2

Methanol (200 mL, 10 vol) was added to Pracinostat form P1 (20 g, 55.79 mmol) in 500 ml round glass flask to give slurry. The slurry was magnetically stirred and heated to 60° C. to give clear solution. The obtained clear solution was stirred at 60° C. during 1 hour and then cooled to room temperature follows by concentration in rotor vapor to give a solid. The obtained solid was dried in a vacuum oven at 25° C. for 18 hours. The obtained crystal solid was characterized by X-ray powder diffractogram to as Pracinostat form P2.

Example 22. Preparation of Pracinostat Form P3

Pracinostat P1 (50 mg) was placed in a glass tube and inserted to a vial filled with various solvents (dimethyl acetamide—DMA, N,N-dimethylformamide—DMF and diacetone alcohol, about 2 ml). The vial was tightly closed for 1 week and after 1 week the sample was characterized by X-ray powder diffractogram.

Example 23. Preparation of Pracinostat Form P3

Pracinostat form P2 (5 g, 13.95 mmol) was dried in vacuum oven at 100° C. for 72 hours. The obtained crystal solid was characterized by X-ray powder diffractogram as Pracinostat form P3.

Example 24. Preparation of Pracinostat Form P3

Methyl isopropyl ketone (300 µL, 10 vol) was added to Pracinostat form P1 (30 mg, 0.084 mmol) in sealed vial to give slurry. The slurry was magnetically stirred at room temperature for 18 hours. The slurry was filtered by centrifugation. The isolated solid was characterized by X-ray powder diffractogram as Pracinostat form P3.

Example 25. Preparation of Pracinostat Form P3

Pracinostat form P1 (500 mg, 1.39 mmol) was added to DMSO (2.5 mL, 5 vol) in a 20 ml vial to give slurry at room temperature. The obtained slurry was magnetically stirred and heated to 60° C. After stirring at 60° C. during 15 minutes, clear solution was obtained. The clear solution was cooled to room temperature and about 140 µl (28 mg, 0.078 mmol) from this clear solution were transferred to another vail. Subsequently, diethyl ether (560 µl, 20 vol) was added gradually to the clear solution at room temperature. The clear solution continued to stir at room temperature during about 1 hour. Next, this clear solution was cooled and stirred at 4° C. for 72 hours to give a precipitation. After that, the obtained precipitant was filtered by centrifugation and characterized by X-ray powder diffractogram as Pracinostat form P3.

Example 26. Preparation of Pracinostat Form P3

2-methoxy ethanol (50 ml, 10 vol) was added to Pracinostat form P2 (5 g, 13.95 mmol) in 250 ml round glass flask to give slurry. The slurry was magnetically stirred at room temperature for 20 minutes to give clear solution. After that, the obtained clear solution was evaporated and the formed solid was dried in vacuum oven at 25° C. for 18 hours. This isolated solid was characterized by X-ray powder diffractogram as Pracinostat form P3.

Example 27. Preparation of Pracinostat Form P3

About 50 mg of Pracinostat form P2 was added to **MEK (500 µL, 10 vol) in 2 ml seal vial. The slurry was magnetically stirred at room temperature for 18 h. The obtained solid was filtered by centrifugation and characterized by X-ray powder diffractogram.
**This process can be done utilizing other organic solvents: ethyl acetate, methyl acetate, isopropyl acetate, propyl acetate, isobutyl acetate, n-butyl acetate, heptane, hexane, pentane, octane, cyclohexane, methyl cyclohexane, toluene, cumene, tetralin, xylene, methyl isobutyl ketone, 2-Me-THF, THF, diethyl ether, anisole, petrolium ether, cyclopentyl methyl ether, 1,1-dimethoxymethane, methyl isopropyl ketone, chlorobenzene, 1,3-dioxolane and MEK (methyl ethyl keton).

Example 28. Preparation of Pracinostat Form P3

Pracinostat form P7 (5 g, 13.95 mmol) was dried in vacuum oven at 100° C. for 1 week. The obtain crystal solid was characterized by X-ray powder diffractogram as Pracinostat form P3.

Example 29. Preparation of Pracinostat Form P3 n-Propanol (300 µL, 10 vol) was added to Pracinostat form P7 (30 mg, 0.084 mmol) in 2 ml sealed vail to give slurry. The obtained slurry was magnetically stirred and heated to 90° C. The slurry was stirred at 90° C. for 18 hours and then filtered by centrifuge. The isolated solid was characterized by X-ray powder diffractogram as Pracinostat form P3.

Example 30. Preparation of Pracinostat Form P3

Isopropyl alcohol (3 mL, 30 vol) was added to Pracinostat Form P1 (100 mg, 0.28 mmol) and immediately heated to 80° C. The mixture was magnetically stirred at 80° C. during about 1 hour to give clear solution follows by mechanically filtration using filter disk. The obtained clear filtrate was cooled to a room temperature and then seeded with Pracinostat Form P3 (about 4-5 dry crystals) to give a turbidity precipitation. The obtained turbid solution was stirred at 4° C. for 4 hours to give massive precipitation. The obtain precipitation was filtrated by centrifugation and characterized by XRD as Pracinostat form P3.

Example 31. Preparation of Pracinostat Form P4

\*\*\*2-propanol (500 µL, 10 vol) was added to Pracinostat form P2 (50 mg, 0.139 mmol) in 2 ml sealed vial to give slurry. The obtained slurry was magnetically stirred at room temperature for 18 hours. Then, the slurry was filtered by centrifugation. The isolated solid was characterized by X-ray powder diffractogram as Pracinostat form P4.
\*\*\*This process can be done utilizing other organic solvents: ethanol, 2-propanol, 2-butanol, propanol, DCM and chloroform.

Example 32. Preparation of Pracinostat Form P4

Chloroform (500 µL, 10 vol) was added to Pracinostat form P2 (50 mg, 0.139 mmol) in 2 ml sealed vail to give slurry. The slurry was magnetically stirred and heated to reflux. The slurry was stirred at reflux during 18 hours and then filtered by centrifugation. The obtained solid was characterized by X-ray powder diffractogram as Pracinostat form P4.

Example 33. Preparation of Pracinostat Form P4

Pracinostat form P4 can be prepared by slurry of Pracinostat form P7 with DCM or chloroform (10 vol) in reflux.
For example: DCM (300 µL, 10 vol) was added to Pracinostat form P7 (30 mg, 0.084 mmol) in 2 ml sealed vial to give slurry. The obtained slurry was magnetically stirred and heated to reflux. The slurry was stirred at reflux for 18 hours and then filtered by centrifugation. The obtained solid was characterized by X-ray powder diffractogram as Pracinostat form P4.

Example 34. Preparation of Pracinostat Form P6

Hexane (300 µL, 10 vol) was added to Pracinostat form P7 (30 mg, 0.084 mmol) in 2 ml sealed vail to give slurry. The obtained slurry was magnetically stirred and heated to reflux. The slurry was stirred at reflux for 18 hours, follows by filtration in centrifuge. The isolated solid was characterized by X-ray powder diffractogram as Pracinostat form P6.

Example 35. Preparation of Pracinostat Form P6

Pracinostat form P6 can be prepared by slurry of Pracinostat form P2 in a mixture of organic solvent (10 vol):water (1 vol) at room temperature. The organic solvent can be isobutyl acetate, n-butyl acetate, heptane, hexane, cumene, xylene, MTBE, diisopropyl ether, diethyl ether and cyclopentylmethyl ether.
For example: DCM (500 µL, 10 vol) and water (50 µL, 1 vol) were added to Pracinostat form P2 (50 mg, 0.139 mmol) to give slurry. The obtained slurry was magnetically stirred at room temperature for 18 hours. The slurry was filtered by centrifugation and the isolated solid was characterized by X-ray powder diffractogram as Pracinostat form P6.

Example 36. Preparation of Pracinostat Form P6

Pracinostat form P6 can be prepared by slurry of Pracinostat form P2 in various organic solvents such as acetonitrile, acetone, tert-butylmethyl ether, diisopropyl ether and 1,1-diethoxypropane).
For example: Acetone (500 µL, 10 vol) was added to Pracinostat form P2 (50 mg, 0.139 mmol) in 2 ml sealed vail to give slurry. The obtained slurry was magnetically stirred at room temperature for 18 hours. Then, the slurry was filtered by centrifugation. The isolated solid was characterized by X-ray powder diffractogram as Pracinostat form P6.

Example 37. Preparation of Pracinostat Form P7

2-ethoxy ethanol (50 ml, 10 vol) was added to Pracinostat form P1 (5 g, 13.95 mmol) in 250 ml round glass flask to give slurry. The obtained slurry was magnetically stirred and heated to 60° C. The stirring at 60° C. was continued over a period of 30 minutes to form a clear solution. This clear solution was cooled to room temperature and stirred at this temperature during 18 hours to give a precipitation. The obtained precipitant was filtrated upon vacuum and dried in vacuum oven at 25° C. for 18 hours. Next, the isolated solid was characterized by X-ray powder diffractogram as Pracinostat form P7.

Example 38. Preparation of Pracinostat Form P7

Isopropyl alcohol (3 mL, 30 vol) was added to Pracinostat Form P1 (100 mg, 0.28 mmol) in a vial of 7 ml to give slurry. The slurry was magnetically stirred and heated to 80° C. The slurry was heated at 80° C. during 1 hour to give clear solution follows by mechanically filtration using filter disk. The obtained clear filtrate was cooled to room temperature and then seeded with Pracinostat Form P7 (about 4-5 dry crystals) to give a turbidity precipitation. The obtained turbid solution was stirred at 4° C. for 4 hours to give massive precipitation. The obtain precipitation was filtered by centrifugation. The isolated solid was characterized by XRD as Pracinostat form P7.

Example 39. Preparation of Pracinostat Form I1—Butyric Acid Solvate

Ethyl Acetate (10.0 ml, 10 vol) and Butyric acid (541.3 µL, 5.9 mmol, 2.1 eq.) were added to Pracinostat form P1 (1.0 g, 2.8 mmol) in 25 ml round flask to prepare slurry. The obtained slurry was magnetically stirred at room temperature for 18 hours follows by vacuum filtration and drying in vacuum oven at 25° C. for about 18 hours. The isolated solid was characterized by X-ray powder diffractogram as Pracinostat Form I1, PXRD pattern is shown in FIG. 23.

Example 40. Preparation of Pracinostat Form I1—Iso-Butyric Acid Solvate

Ethyl acetate (1.0 µL, 10 vol) and iso-butyric acid (63.37 µL, 2.5 eq) were added to Pracinostat form P1 (100 mg, 0.28 mmol) in a vail of 2 ml to give a slurry. The obtained slurry was magnetically stirred at room temperature for 18 hours follows by filtration in centrifuge and drying in vacuum oven at 25° C. for about 18 hours. The isolated solid was characterized by X-ray powder diffractogram as Pracinostat Form I1.

Example 41. Preparation of Pracinostat Form I2—Butyric Acid Solvate

Ethyl Acetate (0.8 ml, 10 vol.) and Butyric acid (43.30 µL, 0.47 mmol, 2.1 eq.) was added to Pracinostat form P7 (80.00 mg, 0.22 mmol) in 1 ml sealed vail to give slurry. The obtained slurry was magnetically stirred at room temperature for 18 hours follows by filtration in centrifuge and drying in vacuum oven at 25° C. for about 18 hours. The isolated solid was characterized by X-ray powder diffractogram as Pracinostat Form I2—solvate of butyric acid (FIG. 24).

Example 42. Preparation of Pracinostat Form I2—Iso-Butyric Acid Solvate

Ethyl Acetate (1.00 ml, 10 vol) and Iso-butyric acid of (63.37 µL, 0.68 mmol, 2.43 eq.) were added to Pracinostat form P7 (100.00 mg, 0.28 mmol) in 1 ml sealed vail to give slurry. The obtained slurry was magnetically stirred at room temperature for 18 hours follows by filtration in centrifuge and drying in vacuum oven at 25° C. for about 18 hours. The isolated solid was characterized by X-ray powder diffractogram as Pracinostat Form I2—solvate of butyric acid Example 43. Preparation of Amorphous Pracinostat Pracinostat (1 g, 2.79 mmol) was dissolved in Methanol (60 mL, 60 vol.) at room temperature. After that, the obtained clear solution was filtered by mechanical filter and concentrated by spray drying at 100° C. for 30 min. The obtained solid was drying in vacuum oven at 25° C. for 18 hours and characterized by X-ray powder diffractogram as Pracinostat amorphous form.

The invention claimed is:

1. A crystalline polymorph of Pracinostat, designated Form P3, characterized by data selected from one or more of the following:
   a) an X-ray powder diffraction pattern substantially as depicted in FIG. 3;
   b) an X-ray powder diffraction pattern having peaks at 5.7, 8.4, 10.2, 14.3 and 15.3 degrees 2-theta±0.2 degrees 2-theta;
   c) a solid state $^{13}$C NMR spectrum substantially as depicted in any one of FIGS. 14a, 14b and 14c;
   d) a solid state $^{13}$C NMR spectrum having peaks at the range of 100-200 ppm at 157.29, 141.28, 137.17, 130.06 and 120.57 ppm±2 ppm;
   e) a solid state $^{13}$C NMR spectrum having the following chemical shift absolute differences from a peak at 165.62 ppm±2 ppm of 8.33, 24.34, 28.45, 35.56 and 45.05±2 ppm;
   f) a solid state $^{13}$C NMR spectrum having chemical shift difference from a peak at 165.62 ppm±1 ppm to 130.06 ppm±1 ppm of 35.36 ppm±1 ppm;
   g) a FTIR spectrum substantially as depicted in FIG. 17; and
   h) combinations of these data.

2. The crystalline polymorph of Pracinostat according to claim 1, characterized by an X-ray powder diffraction pattern having peaks at 5.7, 8.4, 10.2, 14.3 and 15.3 degrees 2-theta±0.2 degrees 2-theta, and also having any one, two, three, four or five additional peaks selected from the group consisting of 16.5, 17.8, 20.1, 20.9 and 23.3 degrees 2-theta±0.2 degrees 2-theta.

3. The crystalline polymorph of Pracinostat according to claim 1, wherein the crystalline form is anhydrous.

4. A crystalline polymorph of Pracinostat according to claim 1, which contains not more than 10% (w/w), of any other crystalline form.

5. A crystalline polymorph of Pracinostat according claim 1, which contains not more than 5% (w/w) of any other crystalline form.

6. A crystalline polymorph of Pracinostat according to claim 1, which contains not more than 1% (w/w) of any other crystalline form.

7. A pharmaceutical formulation comprising any one or a combination of a crystalline polymorph of Pracinostat according claim 1 and at least one pharmaceutically acceptable excipient.

* * * * *